United States Patent [19]

Dowell et al.

[11] Patent Number: 5,225,438

[45] Date of Patent: Jul. 6, 1993

[54] ARYL DERIVATIVES

[75] Inventors: Robert I. Dowell, Congleton; Philip N. Edwards, Bramhall; Keith Oldham, Poynton, all of England

[73] Assignees: Imperial Chemical Industries PLC, London, England; I.C.I.-Pharma, Cedex, France

[21] Appl. No.: 797,898

[22] Filed: Nov. 26, 1991

[30] Foreign Application Priority Data

Nov. 28, 1990 [EP] European Pat. Off. ............ 90403377
Sep. 24, 1991 [EP] European Pat. Off. ............ 91402536

[51] Int. Cl.$^5$ .................. C07D 315/00; C07D 309/12
[52] U.S. Cl. ..................................... 514/459; 514/460; 549/416; 549/417; 549/419; 549/420; 549/423
[58] Field of Search ............... 549/423, 419, 420, 416, 549/417; 514/459, 460

[56] References Cited

U.S. PATENT DOCUMENTS

| | | | |
|---|---|---|---|
| 3,661,917 | 5/1972 | Kaiser et al. | 546/232 |
| 3,743,737 | 7/1973 | Kaiser et al. | 514/331 |
| 4,567,184 | 1/1986 | Musser et al. | 514/277 |
| 4,625,034 | 11/1986 | Neiss et al. | 546/152 |
| 4,631,287 | 12/1988 | Chakraborty et al. | 514/307 |
| 4,725,619 | 2/1988 | Chakraborty | 514/442 |
| 4,728,668 | 3/1988 | Chakraborty et al. | 514/464 |
| 4,794,188 | 12/1988 | Musser et al. | 546/152 |
| 4,839,369 | 5/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |
| 5,098,930 | 3/1992 | Edwards et al. | 549/423 |

FOREIGN PATENT DOCUMENTS

| | | |
|---|---|---|
| 0110405 | 6/1984 | European Pat. Off. |
| 0190722 | 1/1986 | European Pat. Off. |
| 0181568 | 5/1986 | European Pat. Off. |
| 0200101 | 12/1986 | European Pat. Off. |
| 0271287 | 6/1988 | European Pat. Off. |
| 0349062 | 6/1989 | European Pat. Off. |

Primary Examiner—Marianne M. Cintins
Assistant Examiner—Michael B. Hydorn
Attorney, Agent, or Firm—Cushman, Darby & Cushman

[57] ABSTRACT

The invention concerns an aryl derivative of the formula I,

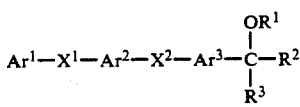

wherein $Ar^1$ is optionally substituted phenyl, naphthyl or a heterocyclic moiety, and $X^1$ is oxy, thio, sulphinyl, sulphonyl, difluoromethylene, imino, (1–4C)alkylimino or optionally substituted (1–4C)alkylene, or $X^1$ is a group of the formula $$-X^4-CR_2- \text{ or } -CR_2-X^4-$$

wherein $X^4$ is oxy, thio, sulphinyl, sulphonyl or carbonyl and each R is hydrogen, methyl or ethyl;

each of $Ar^2$ and $Ar^3$ is optionally substituted phenylene;

$X^2$ is oxy, thio, sulphinyl or sulphonyl;

$R^1$ is (1–4C)alkyl; and $R^2$ and $R^3$ together form a group of the formula $-A^1-X^3-A^2-$ which together with the carbon atom to which $A^1$ and $A^2$ are attached define a ring having 5 to 7 ring atoms, wherein each of $A^1$ and $A^2$ is (1–3C)alkylene and $X^3$ is oxy, thio, sulphinyl or sulphonyl;

which compounds are inhibitors of 5-lipoxygenase and are useful in the treatment of inflammatory or allergic disease.

9 Claims, No Drawings

ARYL DERIVATIVES

This invention concerns novel aryl derivatives and more particularly novel aryl derivatives which are inhibitors of the enzyme 5-lipoxygenase (hereinafter referred to as 5-LO). The invention also concerns processes for the manufacture of said aryl derivatives and novel pharmaceutical compositions containing them. Also included in the invention is the use of said aryl derivatives in the treatment of various inflammatory and/or allergic diseases in which the direct or indirect products of 5-LO catalysed oxidation of arachidonic acid are involved, and the production of new medicaments for such use.

As stated above the aryl derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application Nos 0375404 A2 and 0385662 A2 that certain heterocyclic derivatives possess inhibitory properties against 5-LO. Copending European Patent Applications Nos 90306765.0 and 90310332.3 (published as European Patent Applications Nos. 0409413 and 0420511 respectively) are also concerned with heterocyclic derivatives which possess inhibitory properties against 5-LO. We have now discovered that certain aryl derivatives which possess some structural features which are similar to those of the compounds disclosed in the above-mentioned applications but which possess other structural features, in particular aryl-containing substituents, which were not envisaged in those earlier applications, are effective inhibitors of the enzyme 5-LO and thus of leukotriene biosyntheses. Thus such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided an aryl derivative of the formula I (set out hereinafter) wherein $Ar^1$ is phenyl or naphthyl which may optionally bear one, two or three substituents selected from amino, halogeno, hydroxy, cyano, carboxy, trifluoromethyl, (1–4C)alkyl, (1–4C)alkoxy, (1–4C)alkylamino, di-[(1–4C)alkyl]amino, (1–4C)alkoxycarbonyl, amino-(1–4C)alkyl, hydroxy-(1–4C)alkyl, cyano-(1–4C)alkyl, carboxy-(1–4C)alkyl, (1–4C)alkoxycarbonyl-(1–4C)alkyl, carboxy-(1–4C)alkoxy, (1–4C)alkoxycarbonyl-(1–4C)alkoxy, amino-(2–4C)alkoxy, (1–4C)alkylamino-(2–4C)alkoxy and di-[(1–4C)alkyl]amino-(2–4C)alkoxy, and $X^1$ is oxy, thio, sulphinyl, sulphonyl, difluoromethylene, imino, (1–4C)alkylimino or (1–4C)alkylene and wherein the (1–4C)alkylene group may optionally bear one or two substituents selected from hydroxy, (1–4C)alkyl, (1–4C)alkoxy and phenyl, or $X^1$ is a group of the formula

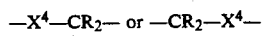

wherein $X^4$ is oxy, thio, sulphinyl, sulphonyl or carbonyl and each R, which may be the same or different, is hydrogen, methyl or ethyl; or wherein $Ar^1$ is a 5- or 6-membered monocyclic heterocyclic moiety or a 9- or 10-membered bicyclic heterocyclic moiety each containing one or two nitrogen heteroatoms and each optionally containing a further heteroatom selected from nitrogen, oxygen and sulphur, or a hydrogenated derivative thereof, which heterocyclic moiety may optionally bear one, two or three substituents selected from halogeno, hydroxy, cyano, trifluoromethyl, oxo, thioxo, (1–4C)alkyl and (1–4C)alkoxy, and $X^1$ is a direct link to $Ar^2$, or $X^1$ is oxy, thio, sulphinyl, sulphonyl, carbonyl or (1–4C)alkylene, and wherein the (1–4C)alkylene group may optionally bear one or two substituents selected from hydroxy, (1–4C)alkyl and (1–4C)alkoxy;

$Ar^2$ and $Ar^3$, which may be the same or different, each is phenylene which may optionally bear one or two substituents selected from halogeno, hydroxy, amino, trifluoromethyl, (1–4C)alkyl and (1–4C)alkoxy;

$X^2$ is oxy, thio, sulphinyl or sulphonyl;

$R^1$ is (1–4C)alkyl, (3–4C)alkenyl or (3–4C)alkynyl; and $R^2$ and $R^3$ together form a group of the formula $-A^1-X^3-A^2-$ which together with the carbon atom to which $A^1$ and $A^2$ are attached define a ring having 5 to 7 ring atoms, wherein $A^1$ and $A^2$, which may be the same or different, each is (1–3C)alkylene and $X^3$ is oxy, thio, sulphinyl or sulphonyl, and which ring may bear one or two substituents selected from hydroxy, (1–4C)alkyl and (1–4C)alkoxy;

or a pharmaceutically-acceptable salt thereof.

According to a further aspect of the invention there is provided an aryl derivative of the formula I as defined hereinbefore wherein $Ar^1$ may optionally bear one, two or three further substituents selected from (1–4C)alkylamino-(1–4C)alkyl and di-[(1–4C)alkyl]amino-(1–4C)alkyl; or a pharmaceutically-acceptable salt thereof.

According to a further aspect the invention there is provided an aryl derivative of the formula I wherein $Ar^1$ is phenyl or naphthyl which may optionally bear one, two or three substituents selected from halogeno, hydroxy, cyano, carboxy, trifluoromethyl, (1–4C)alkyl, (1–4C)alkoxy, (1–4C)alkoxycarbonyl, hydroxy-(1–4C)alkyl, cyano-(1–4C)alkyl, carboxy-(1–4C)alkyl, (1–4C)alkoxycarbonyl-(1–4C)alkyl, carboxy-(1–4C)alkoxy, (1–4C)alkoxycarbonyl-(1–4C)alkoxy, amino-(2–4C)alkoxy, (1–4C)alkylamino-(2–4C)alkoxy and di-

[(1-4C)alkyl]amino-(2-4C)alkoxy, and $X^1$ is oxy, thio, sulphinyl, sulphonyl, difluoromethylene or (1-4C)alkylene and wherein the (1-4C)alkylene group may optionally bear one or two substituents selected from hydroxy, (1-4C)alkyl, (1-4C)alkoxy and phenyl, or $X^1$ is a group of the formula

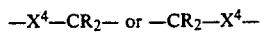

wherein
$X^4$ is oxy, thio, sulphinyl, sulphonyl or carbonyl and each R, which may be the same or different, is hydrogen, methyl or ethyl; or wherein
$Ar^1$ is a 5- or 6-membered monocyclic heterocyclic moiety or a 9- or 10-membered bicyclic heterocyclic moiety each containing one or two nitrogen heteroatoms and each optionally containing a further heteroatom selected from nitrogen, oxygen and sulphur, or a hydrogenated derivative thereof, which heterocyclic moiety may optionally bear one, two or three substituents selected from halogeno, hydroxy, cyano, trifluoromethyl, oxo, thioxo, (1-4C)alkyl and (1-4C)alkoxy, and $X^1$ is a direct link to $Ar^2$, or $X^1$ is oxy, thio, sulphinyl, sulphonyl, carbonyl or (1-4C)alkylene, and wherein the (1-4C)alkylene group may optionally bear one or two substituents selected from hydroxy, (1-4C)alkyl and (1-4C)alkoxy;
$Ar^2$ and $Ar^3$, which may be the same or different, each is phenylene which may optionally bear one or two substituents selected from halogeno, hydroxy, amino, trifluoromethyl, (1-4C)alkyl and (1-4C)alkoxy;
$X^2$ is oxy, thio, sulphinyl or sulphonyl;
$R^1$ is (1-4C)alkyl, (3-4C)alkenyl or (3-4C)alkynyl; and
$R^2$ and $R^3$ together form a group of the formula $-A^1-X^3-A^2-$ which together with the carbon atom to which $A^1$ and $A^2$ are attached define a ring having 5 to 7 ring atoms, wherein $A^1$ and $A^2$, which may be the same or different, each is (1-3C)alkylene and $X^3$ is oxy, thio, sulphinyl or sulphonyl, and which ring may bear one or two substituents selected from hydroxy, (1-4C)alkyl and (1-4C)alkoxy;
or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $Ar^1$ when it is naphthyl is, for example, 1-naphthyl or 2-naphthyl.

Suitable values for substituents which may be present on $Ar^1$, $Ar^2$ or $Ar^3$ include, for example:

| | |
|---|---|
| for halogeno: | fluoro, chloro, bromo and iodo; |
| for (1-4C)alkyl: | methyl, ethyl, propyl, isopropyl, butyl, isobutyl, sec-butyl and tert-butyl; |
| for (1-4C)alkoxy: | methoxy, ethoxy, propoxy, isopropoxy and butoxy; |
| for (1-4C)alkylamino: | methylamino, ethylamino, propylamino and butylamino; |
| for di-[(1-4C)alkyl]amino: | dimethylamino, diethylamino and N-ethyl-N-methylamino; |
| for (1-4C)alkoxycarbonyl: | methoxycarbonyl and ethoxycarbonyl; |
| for amino-(1-4C)alkyl: | aminomethyl, 1-aminoethyl, 2-aminoethyl and 2-aminoprop-2-yl; |
| for (1-4C)alkylamino-(1-4C)-alkyl: | methylaminomethyl, 2-methylaminoethyl, 3-methylaminopropyl and 4-methylaminobutyl; |
| for di-[(1-4C)alkyl]amino-(1-4C)alkyl: | dimethylaminomethyl, 2-dimethylaminoethyl, 3-dimethylaminopropyl and 4-dimethylaminobutyl; |
| for hydroxy-(1-4C)alkyl: | hydroxymethyl, 1-hydroxyethyl and 2-hydroxyprop-2-yl; |
| for cyano-(1-4C)alkyl: | cyanomethyl, 1-cyanoethyl, 2-cyanoethyl and 2-cyanoprop-2-yl; |
| for carboxy-(1-4C)alkyl: | carboxymethyl, 1-carboxyethyl, 2-carboxyethyl and 2-carboxyprop-2-yl; |
| for (1-4C)alkoxycarbonyl-(1-4C)alkyl: | methoxycarbonylmethyl, ethoxycarbonylmethyl, 1-methoxycarbonylethyl, 1-ethoxycarbonylethyl, 2-methoxycarbonylprop-2-yl and 2-ethoxycarbonylprop-2-yl; |
| for carboxy-(1-4C)alkoxy: | carboxymethoxy, 1-carboxyethoxy, 2-carboxyethoxy and 2-carboxyprop-2-yloxy; |
| for (1-4C)alkoxycarbonyl-(1-4C)alkoxy: | methoxycarbonylmethoxy, ethoxycarbonylmethoxy, 1-methoxycarbonylethoxy, 2-methoxycarbonylprop-2-yloxy and 2-ethoxycarbonylprop-2-yloxy; |
| for amino-(2-4C)alkoxy: | 2-aminoethoxy, 2-aminopropoxy and 4-aminobutoxy; |
| for (1-4C)alkylamino-(2-4C)alkoxy: | 2-methylaminoethoxy, 3-methylaminopropoxy and 2-ethylaminoethoxy; |
| for di-[(1-4C)alkyl]amino-(2-4C)alkoxy: | 2-dimethylaminoethoxy, 3-dimethylaminopropoxy and 2-diethylaminoethoxy. |

A suitable value for $X^1$ when it is (1-4C)alkylimino is, for example, methylimino, ethylimino or propylimino.

A suitable value for $X^1$ when it is (1-4C)alkylene is, for example, methylene, ethylene, trimethylene or tetramethylene.

Suitable values for $X^1$ when it is (1-4C)alkylene which bears one or two substituents selected from hydroxy, (1-4C)alkyl, (1-4C)alkoxy and phenyl include, for example, hydroxymethylene, 1-hydroxyethylene, 2-hydroxyethylene, ethylidene, propylidene, isopropylidene, 1-methylethylene, 2-methylethylene, methoxymethylene, ethoxymethylene, 1-methoxyethylene, 2-methoxyethylene, benzylidene, 1-phenylethylene, 2- phenylethylene, 1-hydroxy-1-methylmethylene, alpha-hydroxybenzylidene, 1-methoxy-1-methylmethylene, 1-ethoxy-1-methylmethylene and alpha-methoxybenzylidene.

A suitable value for $Ar^1$ when it is a 5- or 6-membered monocyclic heterocyclic moiety or a 9- or 10-membered bicyclic heterocyclic moeity each containing one or two nitrogen heteroatoms and each optionally containing a further heteroatom selected from nitrogen, oxygen and sulphur, or a hydrogenated derivative thereof, is, for example, pyrrolyl, pyrrolidinyl, indolyl, pyrazolyl, indazolyl, imidazolyl, benzimidazolyl, oxazolyl, isoxazolyl, thiazolyl, isothiazolyl, 1,2,3-triazolyl, 1,2,4-triazolyl, oxadiazolyl, thiadiazolyl, pyridyl, quinolyl, isoquinolyl, pyrazinyl, pyrimidinyl, pyridazinyl, quinoxalinyl, quinazolinyl or cinnolinyl, which may be attached through any available position including through any available nitrogen atom and which may bear one, two or three substituents including a (1–4C)alkyl substituent on any available nitrogen atom. A particular value for $Ar^1$ is such a heterocyclic moiety which bears one oxo or thioxo substituent, for example, 2-oxo-1,2-dihydropyridyl, 4-oxo-1,4-dihydropyridyl, 2-oxo-1,2-dihydroquinolinyl, 4-oxo-1,4-dihydroquinolinyl or 4-oxo-3,4-dihydroquinazolinyl, or the corresponding thioxo derivatives such as 2-thioxo-1,2-dihydropyridyl, which may be attached through any available position including through any available nitrogen atom and which may bear a further substituent including a (1–4C)alkyl substituent on any available nitrogen atom.

A suitable value for $Ar^2$ and $Ar^3$, which may be the same or different, when each is phenylene is, for example, 1,2-phenylene, 1,3-phenylene or 1,4-phenylene.

A suitable value for $R^1$ when it is (1–4C)alkyl is, for example, methyl, ethyl, propyl or butyl; when it is (3–4C)alkenyl is, for example, allyl, 2-butenyl or 3-butenyl; and when it is (3–4C)alkynyl is, for example, 2-propynyl or 2-butynyl.

When $R^2$ and $R^3$ together form a group of the formula $-A^1-X^3-A^2-$ which together with the carbon atom to which $A^1$ and $A^2$ are attached define a ring having 5 to 7 ring atoms then a suitable value for $A^1$ or $A^2$, which may be the same or different, when each is (1–3C)alkylene is, for example, methylene, ethylene or trimethylene. Suitable values for the substituents which may be present on said 5-to 7-membered ring include for example:

| for (1–4C)alkyl: | methyl, ethyl, propyl, isopropyl, butyl and isobutyl; |
|---|---|
| for (1–4C)alkoxy: | methoxy, ethoxy, propoxy, isopropoxy and butoxy. |

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, aryl derivatives of the formula I wherein:

(a) $Ar^1$ is phenyl or naphthyl which may optionally bear one or two substituents selected from amino, halogeno, hydroxy, cyano, carboxy, trifluoromethyl, (1–4C)alkyl, (1–4C)alkoxy, (1–4C)alkylamino, di-[(1–4C)alkyl]amino, amino-(1–4C)alkyl, hydroxy-(1–4C)alkyl, carboxy-(1–4C)alkyl, carboxy-(1–4C)alkoxy and di-[(1–4C)alkyl]amino-(2–4C)alkoxy, and $X^1$ is oxy, thio, sulphinyl, sulphonyl, difluoromethylene, imino or (1–4C)alkylene, and wherein the (1–4C)alkylene group may optionally bear one or two substituents selected from hydroxy, (1–4C)alkyl, (1–4C)alkoxy, and phenyl, or $X^1$ is a group of the formula $$-X^4-CR_2-$$

wherein $X^4$ is oxy, thio, sulphinyl or sulphonyl and each R, which may be the same or different, is hydrogen or methyl; and $Ar^2$, $X^2$, $Ar^3$, $R^1$, $R^2$ and $R^3$ have any of the meanings defined hereinbefore;

(b) $Ar^1$ is phenyl or naphthyl which may optionally bear one or two substituents selected from halogeno, hydroxy, carboxy, trifluoromethyl, (1–4C)alkyl, (1–4C)alkoxy, hydroxy-(1–4C)alkyl, carboxy-(1–4C)alkyl, carboxy-(1–4C)alkoxy and di-[(1–4C)alkyl]amino-(2–4C)alkoxy, and $X^1$ is thio, sulphinyl, sulphonyl, difluoromethylene or (1–4C)alkylene, and wherein the (1–4C)alkylene group may optionally bear one or two substituents selected from hydroxy, (1–4C)alkyl, (1–4C)alkoxy and phenyl, or $X^1$ is a group of the formula $$-X^4-CR_2-$$

wherein $X^4$ is oxy, thio, sulphinyl or sulphonyl and each R, which may be the same or different, is hydrogen or methyl; and $Ar^2$, $X^2$, $Ar^3$, $R^1$, $R^2$ and $R^3$ have any of the meanings defined hereinbefore;

(c) $Ar^1$ is phenyl which may optionally bear one or two substituents selected from halogeno, trifluoromethyl, cyano, (1–4C)alkyl, di-[(1–4C)alkyl]amino, amino-(1–4C)alkyl and di-[(1–4C)alkyl]amino-(2–4C)alkoxy, and $X^1$ is oxy, thio, sulphinyl, sulphonyl, difluoromethylene, oxymethylene or methylene, and wherein the methylene group may optionally bear one or two substituents selected from hydroxy, (1–4C)alkyl, (1–4C)alkoxy and phenyl; and $Ar^2$, $X^2$, $Ar^3$, $R^1$, $R^2$ and $R^3$ have any of the meanings defined hereinbefore;

(d) $Ar^1$ is phenyl which may optionally bear one or two substituents selected from halogeno, trifluoromethyl, cyano, (1–4C)alkyl, di-[(1–4C)alkyl]amino, amino-(1–4C)alkyl, (1–4C)alkylamino-(1–4C)alkyl, di-[(1–4C)]alkylamino-(1–4C)alkyl and di-[(1–4C)alkyl]amino-(2–4C)alkoxy, and $X^1$ is oxy, thio, sulphinyl, sulphonyl, difluoromethylene, oxymethylene or methylene, and wherein the methylene group may optionally bear one or two substituents selected from hydroxy, (1–4C)alkyl, (1–4C)alkoxy and phenyl; and $Ar^2$, $X^2$, $Ar^3$, $R^1$, $R^2$ and $R^3$ have any of the meanings defined hereinbefore;

(e) $Ar^1$ is phenyl or 2-naphthyl which may optionally bear one or two substituents selected from halogeno, trifluoromethyl and (1–4C)alkyl, and $X^1$ is thio, sulphinyl, sulphonyl, difluoromethylene, oxymethylene or (1–4C)alkylene, and wherein the (1–4C)alkylene group may optionally bear one or two substituents selected from hydroxy, (1–4C)alkyl, (1–4C)alkoxy and phenyl; and $Ar^2$, $X^2$, $Ar^3$, $R^1$, $R^2$ and $R^3$ have any of the meanings defined hereinbefore;

(f) $Ar^1$ is a 5- or 6-membered monocyclic heterocyclic moiety each containing one or two nitrogen heteroatoms and each optionally containing a further heteroatom selected from nitrogen, oxygen and sulphur, or a hydrogenated derivative thereof, which heterocyclic moiety may optionally bear one or two substituents selected from halogeno, hydroxy, oxo and (1–4C)alkyl, and $X^1$ is a direct link to $Ar^2$, or $X^1$ is carbonyl or (1–4C)alkylene and wherein the (1–4C)alkylene group may optionally bear one or two substituents selected from hydroxy, (1–4C)alkyl and (1–4C)alkoxy; and $Ar^2$, $X^2$, $Ar^3$, $R^1$, $R^2$ and $R^3$ have any of the meanings defined hereinbefore;

(g) $Ar^2$ is 1,3-phenylene or 1,4-phenylene which may optionally bear one substituent selected from halogeno, (1–4C)alkyl and (1–4C)alkoxy; and $Ar^1$, $X^1$, $X^2$, $Ar^3$, $R^1$, $R^2$ and $R^3$ have any of the meanings defined hereinbefore;

(h) $X^2$ is thio, sulphinyl or sulphonyl; and $Ar^1$, $X^1$, $Ar^2$, $Ar^3$, $R^1$, $R^2$ and $R^3$ have any of the meanings defined hereinbefore;

(i) $Ar^3$ is 1,3-phenylene or 1,4-phenylene which may optionally bear one or two substituents selected from halogeno, amino, trifluoromethyl, (1–4C)alkyl and (1–4C)alkoxy; and $Ar^1$, $X^1$, $Ar^2$, $X^2$, $R^1$, $R^2$ and $R^3$ have any of the meanings defined hereinbefore;

(j) $R^1$ is (1–4C)alkyl; and $Ar^1$, $X^1$, $Ar^2$, $X^2$, $Ar^3$, $R^2$ and $R^3$ have any of the meanings defined hereinbefore; and (k) $R^2$ and $R^3$ together form a group of the formula $-A^1-X^3-A^2-$ which together with the carbon atom to which $A^1$ and $A^2$ are attached define a ring having 5 or 6 ring atoms, wherein $A^1$ and $A^2$, which may be the same or different, each is (1–3C)alkylene and $X^3$ is oxy, and which ring bear one or two (1–4C)alkyl substituents; and $Ar^1$, $X^1$, $Ar^2$, $X^2$, $Ar^3$ and $R^1$ have any of the meanings defined hereinbefore;

or a pharmaceutically-acceptable salt thereof.

A further particular compound of the invention comprises an aryl derivative of the formula I wherein $Ar^1$ is phenyl which may optionally bear one or two substituents selected from fluoro, chloro, hydroxy, cyano, trifluoromethyl, methyl, ethyl, tert-butyl, methoxy, ethoxy, methylamino, ethylamino, dimethylamino, diethylamino, aminomethyl, hydroxymethyl, 2-hydroxyprop-2-yl, carboxymethyl, 1-carboxyethyl, 2-carboxyprop-2-yl, carboxymethoxy, 1-carboxyethoxy, 2-carboxyprop-2-yloxy, 2-dimethylaminoethoxy and 3-dimethylaminopropoxy;

$X^1$ is oxy, thio, sulphinyl, sulphonyl, difluoromethylene, imino, methylene, hydroxymethylene, ethylidene, methoxymethylene, benzylidene, 1-hydroxy-1-methylmethylene, alpha-hydroxybenzylidene or 1-methoxy-1-methylmethylene, or $X^1$ is a group of the formula $$-X^4-CH_2-$$

wherein $X^4$ is oxy, thio, sulphinyl or sulphonyl;

$Ar^2$ is 1,4-phenylene which may optionally bear one substituent selected from fluoro, chloro, methyl and methoxy;

$X^2$ is oxy, thio, sulphinyl or sulphonyl;

$Ar^3$ is 1,3-phenylene which may optionally bear one or two substituents selected from fluoro, chloro, trifluoromethyl and methyl;

$R^1$ is methyl or ethyl; and $R^2$ and $R^3$ together form a group of the formula $-A^1-X^3-A^2-$ which together with the carbon atom to which $A^1$ and $A^2$ are attached define a ring having 6 ring atoms, wherein $A^1$ is ethylene, $A^2$ is ethylene and $X^3$ is oxy, and which ring may bear one or two methyl substituents;

or a pharmaceutically-acceptable salt thereof.

A further particular compound of the invention comprises an aryl derivative of the formula I as defined immediately hereinbefore wherein $Ar^1$ may optionally bear one or two further substituents selected from methylaminomethyl, 2-methylaminoethyl, 3-methylaminopropyl, dimethylaminomethyl, 2-dimethylaminoethyl and 3-dimethylaminopropyl;

or a pharmaceutically-acceptable salt thereof.

A further particular compound of the invention comprises an aryl derivative of the formula I wherein $Ar^1$ is phenyl which may optionally bear one or two substituents selected from fluoro, chloro, hydroxy, carboxy, trifluoromethyl, methyl, ethyl, tert-butyl, methoxy, ethoxy, hydroxymethyl, 2-hydroxyprop-2-yl, carboxymethyl, 1-carboxyethyl, 2-carboxyprop-2-yl, carboxymethoxy, 1-carboxyethoxy, 2-carboxyprop-2-yloxy and 2-dimethylaminoethoxy;

$X^1$ is thio, sulphinyl, sulphonyl, difluoromethylene, methylene, ethylene, hydroxymethylene, ethylidene, methoxymethylene, benzylidene, 1-hydroxy-1-methylmethylene, alpha-hydroxybenzylidene or 1-methoxy-1-methylmethylene, or $X^1$ is a group of the formula $$-X^4-CH_2-$$

wherein $X^4$ is oxy, thio, sulphinyl or sulphonyl;

$Ar^2$ is 1,4-phenylene which may optionally bear one substituent selected from fluoro, chloro, methyl and methoxy;

$X^2$ is thio;

$Ar^3$ is 1,3-phenylene which may optionally bear one or two substituents selected from fluoro, chloro, trifluoromethyl and methyl;

$R^1$ is methyl or ethyl; and $R^2$ and $R^3$ together form a group of the formula $-A^1-X^3-A^2-$ which together with the carbon atom to which $A^1$ and $A^2$ are attached define a ring having 6 ring atoms, wherein $A^1$ is ethylene, $A^2$ is ethylene and $X^3$ is oxy, and which ring may bear one or two methyl substituents;

or a pharmaceutically-acceptable salt thereof.

A further particular compound of the invention comprises an aryl derivative of the formula I wherein $Ar^1$ is phenyl which may optionally bear one or two substituents selected from fluoro, chloro, trifluoromethyl, cyano, methyl, ethyl, tert-butyl, methylamino, dimethylamino, aminomethyl, carboxymethoxy, 2-dimethylaminoethoxy and 3-dimethylaminopropoxy;

$X^1$ is oxy, thio, sulphinyl, sulphonyl, difluoromethylene, imino, oxymethylene, methylene, hydroxymethylene, ethylidene, methoxymethylene, benzylidene, 1-hydroxy-1-methylmethylene, alpha-hydroxybenzylidene or 1-methoxy-1-methylmethylene;

Ar$^2$ is 1,4-phenylene which may optionally bear one substituent selected from fluoro, chloro, methyl and methoxy;

X$^2$ is oxy, thio or sulphonyl;

Ar$^3$ is 1,3-phenylene which may optionally bear one or two substituents selected from fluoro, chloro, trifluoromethyl and methyl;

R$^1$ is methyl or ethyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ is ethylene, A$^2$ is ethylene and X$^3$ is oxy, and which ring may bear one or two methyl substituents; or a pharmaceutically-acceptable salt thereof.

A further particular compound of the invention comprises an aryl derivative of the formula I wherein Ar$^1$ is phenyl which may optionally bear one or two substituents selected from fluoro, chloro, trifluoromethyl, methyl, ethyl and tert-butyl;

X$^1$ is thio, sulphinyl, sulphonyl, difluoromethylene, oxymethylene, methylene, ethylene, hydroxymethylene, ethylidene, methoxymethylene, benzylidene, 1-hydroxy-1-methylmethylene, alpha-hydroxybenzylidene or 1-methoxy-1-methylmethylene;

Ar$^2$ is 1,4-phenylene which may optionally bear one substituent selected from fluoro, chloro, methyl and methoxy;

X$^2$ is thio;

Ar$^3$ is 1,3-phenylene which may optionally bear one or two substituents selected from fluoro, chloro, trifluoromethyl and methyl;

R$^1$ is methyl or ethyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ is ethylene, A$^2$ is ethylene and X$^3$ is oxy, and which ring may bear one or two methyl substituents; or a pharmaceutically-acceptable salt thereof.

A further particular compound of the invention comprises an aryl derivative of the formula I wherein Ar$^1$ is 1-pyrrolyl, 1-pyrazolyl, 3-pyridyl, 2-oxo-1,2-dihydropyrid-1-yl or 4-oxo-1,4-dihydropyrid-1-yl;

X$^1$ is a direct link to Ar$^2$, or X$^1$ is carbonyl or methylene;

Ar$^2$ is 1,4-phenylene which may optionally bear one substituent selected from fluoro, chloro, methyl and methoxy;

X$^2$ is thio;

Ar$^3$ is 1,3-phenylene which may optionally bear one or two substituents selected from fluoro, chloro, trifluoromethyl and methyl;

R$^1$ is methyl or ethyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ is ethylene, A$^2$ is ethylene and X$^3$ is oxy, and which ring may bear one or two methyl substituents; or a pharmaceutically-acceptable salt thereof.

A preferred compound of the invention comprises an aryl derivative of the formula I wherein Ar$^1$ is phenyl, 4-fluorophenyl, 2,4-difluorophenyl, 2,6-dichlorophenyl or 4-dimethylaminophenyl;

X$^1$ is oxy, thio, oxymethylene, methylene, ethylidene or difluoromethylene;

Ar$^2$ is 1,4-phenylene or 2-chloro-1,4-phenylene;

X$^2$ is thio;

Ar$^3$ is 1,3-phenylene or 5-fluoro-1,3-phenylene;

R$^1$ is methyl; and

R$^2$ and R$^3$ together form a group of the formula —A$^1$—X$^3$—A$^2$— which together with the carbon atom to which A$^1$ and A$^2$ is attached define a ring having 6 ring atoms, wherein A$^1$ is ethylene, A$^2$ is ethylene and X$^3$ is oxy, and which ring may bear a methyl substituent alpha to X$^3$;

or a pharmaceutically-acceptable salt thereof.

A further preferred compound of the invention comprises an aryl derivative of the formula I wherein Ar$^1$ is 4-fluorophenyl, 2,4-difluorophenyl or 2,6-dichlorophenyl;

X$^1$ is oxymethylene, methylene, ethylidene or difluoromethylene;

Ar$^2$ is 1,4-phenylene;

X$^2$ is thio;

Ar$^3$ is 1,3-phenylene or 5-fluoro-1,3-phenylene;

R$^1$ is methyl; and

R$^2$ and R$^3$ together form a group of the formula —A$^1$—X$^3$—A$^2$— which together with the carbon atom to which A$^1$ and A$^2$ is attached define a ring having 6 ring atoms, wherein A$^1$ is ethylene, A$^2$ is ethylene and X$^3$ is oxy, and which ring may bear a methyl substituent alpha to X$^3$; or a pharmaceutically-acceptable salt thereof.

A further preferred compound of the invention comprises an aryl derivative of the formula I wherein Ar$^1$ is 1-pyrrolyl or 3-pyridyl;

X$^1$ is a direct link to Ar$^2$, or X$^1$ is carbonyl or methylene;

Ar$^2$ is 1,4-phenylene;

X$^2$ is thio;

Ar$^3$ is 1,3-phenylene or 5-fluoro-1,3-phenylene;

R$^1$ is methyl; and

R$^2$ and R$^3$ together form a group of the formula —A$^1$—X$^3$—A$^2$— which together with the carbon atom to which A$^1$ and A$^2$ is attached define a ring having 6 ring atoms, wherein A$^1$ is ethylene, A$^2$ is ethylene and X$^3$ is oxy, and which ring may bear a methyl substituent alpha to X$^3$;

or a pharmaceutically-acceptable salt thereof.

A specific especially preferred compound of the invention is, for example, the following aryl derivative of the formula I, or a pharmaceutically-acceptable salt thereof:

4-[3-(4-(4-fluorobenzyl)phenylthio)phenyl]-4-methoxytetrahydropyran,

4-[3-(4-(2,4-difluorobenzyl)phenylthio)phenyl]-4-methoxytetrahydropyran,

4-[3-(4-(4-fluoro-alpha-methylbenzyl)phenylthio)phenyl]-4-methoxytetrahydropyran, 4-[3-(4-(4-fluorophenoxymethyl)phenylthio)phenyl]-4-methoxytetrahydropyran, 4-[5-fluoro-3-(4-(4-fluoro-alpha,alpha-difluorobenzyl)phenylthio)phenyl]-4-methoxytetrahydropyran, 4-[3-(4-(4-fluorophenylthio)phenylthio)phenyl]-4-methoxytetrahydropyran, 4-[5-fluoro-3-(4-phenoxyphenylthio)phenyl]-4-methoxytetrahydropyran or 4-[5-fluoro-3-(3-chloro-4-(4-fluorophenoxy)phenylthio)phenyl]-4-methoxytetrahydropyran.

A further specific especially preferred compound of the invention is, for example, the following aryl derivative of the formula I, or a pharmaceutically-acceptable salt thereof:

4-methoxy-4-[3-(4-(pyrrol-1-ylmethyl)phenylthio)phenyl]tetrahydropyran.

A compound of the invention comprising an aryl derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $X^1$, $Ar^2$, $X^2$, $Ar^3$, $R^1$, $R^2$ and $R^3$ have any of the meanings defined hereinbefore.

(a) The coupling, conveniently in the presence of a suitable base, of a compound of the formula $Ar^1$—$X^1$—$Ar^2$—$X^2$—H with a compound of the formula II wherein Z is a displaceable group; provided that, when there is an amino, imino, alkylamino, carboxy or hydroxy group in $Ar^1$, $X^1$, $Ar^2$, $Ar^3$, $R^2$ or $R^3$, any amino, imino, alkylamino, carboxy or hydroxy group may be protected by a conventional protecting group or alternatively any such group need not be protected; whereafter any undesired protecting group in $Ar^1$, $X^1$, $Ar^2$, $Ar^3$, $R^2$ or $R^3$ is removed by conventional means.

A suitable displaceable group Z is, for example, a halogeno or sulphonyloxy group, for example a chloro, bromo, iodo, methanesulphonyloxy or toluene-4-sulphonyloxy group.

A suitable base for the coupling reaction is, for example, an alkali or alkaline earth metal carbonate, (1–4C-)alkoxide, hydroxide or hydride, for example sodium carbonate, potassium carbonate, sodium ethoxide, potassium butoxide, sodium hydroxide, potassium hydroxide, sodium hydride or potassium hydride. The coupling reaction is conveniently performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)-palladium, cuprous chloride or cuprous bromide.

A suitable protecting group for an amino, imino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) which may be removed, for example, by hydrolysis with a suitable base such as an alkali metal hydroxide, for example lithium or sodium hydroxide; or, for example, a tert-butyl group which may be removed, for example, by treatment with a suitable acid such as hydrochloric, sulphuric or phosphoric acid or trifluoroacetic acid.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Ar^1$—$X^1$—$Ar^2$—$X^2$—H and of the formula II may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Conveniently intermediates of the formula II wherein Z, $Ar^3$, $R^1$, $R^2$ and $R^3$ have the meanings defined hereinbefore, may be obtained by way of compounds of the formula Z—$Ar^3$—Y, wherein Z and $Ar^3$ have the meanings defined hereinbefore and Y is, for example, a halogeno, formyl, alkanoyl, nitrile or alkoxycarbonyl group, as illustrated in accompanying Scheme I (set out hereinafter). Thus, for example, in the accompanying non-limiting Examples it is shown how to convert a compound of the formula Z—$Ar^3$—Y wherein Y is a halogeno group to a compound of the formula II.

It will also be appreciated that the intermediate of the formula II may conveniently be obtained from the compound of the formula Z—$Ar^3$—Y, as defined hereinbefore, by reversing the order of introduction of the groups $R^2$ and $R^3$ which is used in Scheme I.

(b) The coupling, conveniently in the presence of a suitable base as defined hereinbefore, of a compound of the formula III with a compound of the formula $Ar^1$—$X^1$—$Ar^2$—Z wherein Z is a displaceable group as defined hereinbefore; provided that, when there is an amino, imino, alkylamino, carboxy or hydroxy group in $Ar^1$, $X^1$, $Ar^2$, $Ar^3$, $R^2$ or $R^3$, any amino, imino, alkylamino, carboxy or hydroxy group may be protected by a conventional protecting group as defined hereinbefore or alternatively any such group need not be protected; whereafter any undesired protecting group in $Ar^1$, $X^1$, $Ar^2$, $Ar^3$, $R^2$ or $R^3$ is removed by conventional means.

The coupling reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula $Ar^1$—$X^1$—$Ar^2$—Z and of the formula III may be obtained by standard procedures of organic chemistry. The preparation of such starting materials is described within the accompanying non-limiting Examples which are provided for the purpose of illustration only. Alternatively necessary starting materials are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group as defined hereinbefore. Examples of such groups are given in Scheme II. The conditions for the introduction and removal of such protecting groups are described in standard textbooks of organic chemistry such as, for example, "Protective Groups in Organic Synthesis" by T. W. Green (J. Wiley and Sons, 1981).

(c) The alkylation, conveniently in the presence of a suitable base as defined hereinbefore, of a compound of the formula IV with a compound of the formula $R^1-Z$, wherein $R^1$ and Z have the meanings defined hereinbefore; provided that, when there is an amino, imino, alkylamino, carboxy or hydroxy group in $Ar^1$, $X^1$, $Ar^2$, $Ar^3$, $R^2$ or $R^3$ any amino, imino, alkylamino, carboxy or hydroxy group may be protected by a conventional protecting group or alternatively any such group need not be protected; whereafter any undesired protecting group in $Ar^1$, $X^1$, $Ar^2$ $Ar^3$, $R^2$ or $R^3$ is removed by conventional means.

The alkylation reaction is conveniently performed in a suitable inert solvent or diluent as defined hereinbefore and at a temperature in the range, for example, 0° to 100° C., conveniently at or near ambient temperature.

The tertiary alcohol starting material of the formula IV may be obtained by standard procedures of organic chemistry. Conveniently, and as illustrated in accompanying Scheme III (set out hereinafter), intermediates of the formulae $Ar^1-X^1-Ar^2-X^2-Ar^3-Y$, wherein $Ar^1$, $X^1$, $Ar^2$, $X^2$ and $Ar^3$ have the meanings defined hereinbefore and Y is, for example, a halogeno, formyl, alkanoyl, nitrile or alkoxycarbonyl group may be utilised in the preparation of the tertiary alcohol starting material of the formula IV.

(d) For the production of those compounds of the formula I wherein $X^1$ or $X^2$ is a sulphinyl or sulphonyl group, $X^1$ contains a sulphinyl or sulphonyl group, or wherein $R^2$ and $R^3$ together form a group of the formula $-A^1-X^3-A^2-$ and $X^3$ is a sulphinyl or sulphonyl group, the oxidation of a compound of the formula I wherein $X^1$ or $X^2$ is a thio group, $X^1$ contains a thio group, or wherein $R^2$ and $R^3$ together form a group of the formula $-A^1-X^3-A^2-$ and $X^3$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formula IV and these are provided as a further feature of the invention.

As stated previously, the novel compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (*Prostaglandins, Leukotrienes Med.*, 1986, 22, 57; *Prostaglandins*, 1984, 28, 666; *Brit. J. Pharmacol.*, 1985, 84, 34P) which involves the use of a protein-$LTB_4$ conjugate produced using the procedure of Young et alia (Prostaglandins, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)-c):

Test a):
  $IC_{50}$ ($LTB_4$) in the range, for example, 0.01-40 $\mu M$
  $IC_{50}$ ($TxB_2$) in the range, for example, 40-200 $\mu M$;

Test b):
  oral $ED_{50}(LTB_4)$ in the range, for example, 1-100 mg/kg;

Test c):
  oral $ED_{50}(LTB_4)$ in the range, for example, 0.5-50 mg/kg.

No overt toxicity or other untoward effects are present in tests b) and/or c) when compounds of the formula I are administered at several multiples of their minimum inhibitory dose or concentration.

Thus, by way of example, the compound 4-[3-(4-(4-fluorobenzyl)phenylthio)phenyl]-4-methoxytetrahydropyran has an $IC_{50}$ of 0.04 $\mu M$ against $LTB_4$ in test a), and an oral $ED_{50}$ of 2 mg/kg versus $LTB_4$ in test c); and the compound 4-[5-fluoro-3-(4-(4-fluoro-alpha,alpha-difluorobenzyl)phenylthio)phenyl]-4-methoxytetrahydropyran has an $IC_{50}$ of 0.14 $\mu M$ against $LTB_4$ in test a), and an oral $ED_{50}$ of 1 mg/kg versus $LTB_4$ in test c). In general those compounds of the formula I which are particularly preferred have an $IC_{50}$ of <1 $\mu M$ against $LTB_4$ in test a), and an oral $ED_{50}$ of <100 mg/kg against $LTB_4$ in tests b) and/or c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises an aryl derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository: for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an aryl derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an aryl derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicyclic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an aryl derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the structures of the end-products of the formula I were confirmed by NMR and mass spectral techniques: unless otherwise stated, $CDCl_3$ solutions of the end-products of the formula I were used for the determination of the NMR spectral data, chemical shift values were measured on the delta scale;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture; and (viii) the following abbreviations have been used:
THF: tetrahydrofuran;
DMF: N,N-dimethylformamide.

EXAMPLE 1

A mixture of 4-fluoro-4'-iododiphenylmethane (2.3 g), 4-(3-mercaptophenyl)-4-methoxytetrahydropyran (1.6 g), cuprous chloride (0.2 g), potassium carbonate (1 g) and DMF (5 ml) was heated to 120° C. for 90 minutes. The mixture was cooled to ambient temperature and partitioned between water and diethyl ether. The organic phase was washed with water and with brine, dried ($MgSO_4$) and evaporated. The residue was purified by medium pressure liquid chromatography using increasingly polar mixtures of hexane and ethyl acetate as eluent. There was thus obtained 4-[3-(4-(4-fluorobenzyl)phenylthio)phenyl]-4-methoxytetrahydropyran (1.4 g, 47%), m.p. 71°–73° C. (recrystallised from a mixture of hexane and diethyl ether).

NMR Spectrum 1.95(m, 4H), 2.95(s, 3H), 3.8(m, 4H), 3.95(s, 2H), 6.9–7.4(m, 12H).

The 4-fluoro-4'-iododiphenylmethane used as a starting material was obtained as follows:

A solution of 1,4-diiodobenzene (12 g) in THF (120 ml) was cooled to −80° C. under an atmosphere of argon and n-butyl lithium (1.6M in hexane, 23 ml) was added dropwise. The mixture was stirred at −80° C. for 30 minutes and then 4-fluorobenzaldehyde (4.6 g) was added dropwise. The mixture was stirred at −80° C. for 30 minutes. Brine (100 ml) was added and the mixture was allowed to warm to ambient temperature. The mixture was extracted with diethyl ether. The organic phase was dried ($MgSO_4$) and evaporated to give 4-fluoro-4'-iododiphenylmethanol as an oil (13.4 g) which was used without further purification.

Potassium iodide (13.5 g) and trimethylsilyl chloride (10 ml) were added in turn to a solution of 4-fluoro-4'-iododiphenylmethanol (6.7 g) in acetonitrile (70 ml) and the mixture was stirred at ambient temperature for 1 hour. The mixture was partitioned between diethyl ether and water. The organic layer was washed with a saturated aqueous sodium sulphite solution, dried ($MgSO_4$) and evaporated. The residue was purified by column chromatography using increasingly polar mixtures of hexane and ethyl acetate as eluent. There was thus obtained the required starting material as a solid (3 g).

NMR Spectrum 3.85(s, 2H), 6.9–7.0(m, 4H), 7.1(m, 2H), 7.6(m, 2H).

The 4-(3-mercaptophenyl)-4-methoxytetrahydropyran used as a starting material was obtained by appropriate repetition of the procedure described below:

A solution of 1,3-dibromobenzene (23.8 g) in THF (120 ml) was cooled to −78° C. under an atmosphere of argon and n-butyl lithium (1.6M in hexane, 62.5 ml) was added dropwise. The mixture was stirred at −78° C. for 30 minutes and a solution of tetrahydropyran-4-one (10 g) in THF (40 ml) was added. The resultant suspension was stirred at −78° C. for 1 hour, allowed to warm to ambient temperature and then stirred for 30 minutes. The mixture was poured into brine (250 ml) and extracted with diethyl ether. The organic phase was dried ($MgSO_4$) and evaporated. The residue was triturated under hexane and the resultant solid (16.8 g) was filtered off.

A solution of the product so obtained in DMF (100 ml) was added dropwise to a slurry of sodium hydride (60% w/w dispersion in mineral oil; 5.25 g) in DMF (10 ml) and the mixture was stirred at ambient temperature for 90 minutes. Methyl iodide (36.5 g) was added and the mixture was stirred at ambient temperature for 16 hours. Ethanol (2 ml) and water (500 ml) were added in turn and the mixture was extracted with diethyl ether (3×200 ml). The combined extracts were washed with water, dried ($MgSO_4$) and evaporated. The residue was purified by column chromatography using increasingly polar mixtures of hexane and ethyl acetate as eluent. There was thus obtained 4-(3-bromophenyl)-4-methoxytetrahydropyran (12 g, 44%) as an oil.

NMR Spectrum 1.88-2.1 (m, 4H), 3.0(s, 3H), 3.78-3.95(m, 4H), 7.2-7.35(m, 2H), 7.42(m, 1H), 7.55(m, 1H).

A solution of a portion (1 g) of the product so obtained in THF (4 ml) was cooled to −80° C. under an atmosphere of argon and n-butyl lithium (1.6M in hexane, 2.4 ml) was added dropwise. The mixture was stirred at −80° C. for 30 minutes, sulphur (0.12 g) was added and the mixture was stirred at −80° C. for a further 30 minutes. Water (10 ml) was added and the mixture was allowed to warm to ambient temperature. The mixture was extracted with diethyl ether (10 ml). The aqueous phase was acidified to pH4 by the addition of dilute aqueous hydrochloric acid solution and extracted with diethyl ether (2×10 ml). The combined organic extracts were dried (MgSO4) and evaporated. There was thus obtained the required starting material as an oil (0.5 g) which crystallised on standing and was used without further purification.

EXAMPLE 2

Using a similar procedure to that described in Example 1 except that the appropriate iodobenzene was used in place of 4-fluoro-4'-iododiphenylmethane there were obtained the compounds described in the following table:

TABLE I

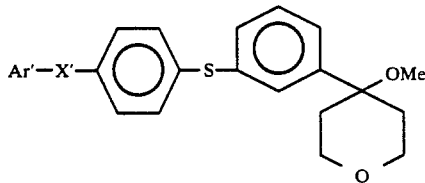

| Ex. 2 Compd. No. | Ar¹ | X¹ | m.p. (°C.) | Yield (%) |
|---|---|---|---|---|
| 1ª | 2,4-difluorophenyl | CH2 | 60–62 | 35 |
| 2ᵇ | 2-chlorophenyl | CH2 | oil | 46 |
| 3ᶜ | 2,6-dichorophenyl | CH2 | oil | 60 |
| 4ᵈ | 4-tert-butylphenyl | CH2 | oil | 40 |
| 5ᵉ | 4-trifluoromethyl-phenyl | CH2 | oil | 40 |
| 6ᶠ | 2-naphthyl | CH2 | oil | 56 |
| 7ᵍ | 4-fluorophenyl | CH(Me) | gum | 42 |
| 8ʰ | phenyl | CH(Ph) | oil | 60 |
| 9ⁱ | phenyl | S | gum | 37 |
| 10ʲ | phenyl | SO2 | 120–122 | 33 |
| 11ᵏ | 4-fluorophenyl | OCH2 | gum | 38 |
| 12ˡ | 4-fluorophenyl | CF2 | 87–89 | 37 |
| 13ᵐ | phenyl | C(OH)(Ph) | oil | 57 |

Notes a. The product gave the following characteristic NMR signals: 1.95(m, 4H), 2.95(s, 3H), 3.8(m, 4H), 3.95(m, 2H), 6.8-7.3(m, 11H).

The 2,4-difluoro-4'-iododiphenylmethane used as a starting material was obtained using the procedures described in Example 1 for the preparation of 4-fluoro-4'-iododiphenylmethane except that 2,4-difluorobenzaldehyde was used in place of 4-fluorobenzaldehyde.

b. The product gave the following characteristic NMR signals: 1.95(m, 4H), 2.95(s, 3H), 3.8(m, 4H), 4.1(s, 2H), 7.1-7.4(m, 12).

The 2-chloro-4'-iododiphenylmethane used as a starting material was obtained using the procedures described in Example 1 for the preparation of 4-fluoro-4'-iododiphenylmethane except that 2-chlorobenzaldehyde was used in place of 4-fluorobenzaldehyde.

c. The product gave the following characteristic NMR signals: 1.9(m, 4H), 2.95(s, 3H), 3.8(m, 4H), 4.3(s, 2H), 7.1-7.3(m, 11H).

The 2,6-dichloro-4'-iododiphenylmethane used as a starting material was obtained using the procedures described in Example 1 for the preparation of 2-fluoro-4'-iododiphenylmethane except that 2,6-dichlorobenzaldehyde was used in place of 4-fluorobenzaldehyde.

d. The product gave the following characteristic NMR signals: 1.3(s, 9H), 1.95(m, 4H), 2.95(s, 3H), 3.8(m, 4H), 3.95(s, 2H), 7.1-7.3(m, 12H).

The 4-tert-butyl-4'-iododiphenylmethane used as a starting material was obtained using the procedures described in Example 1 for the preparation of 4-fluoro-4'-iododiphenylmethane except that 4-tert-butylbenzaldehyde was used in place of 4-fluorobenzaldehyde.

e. The product gave the following characteristic NMR signals: 1.95(m, 4H), 2.95(s, 3H), 3.8(m, 4H), 4.0(s, 2H), 7.1-7.55(m, 12H).

The 4-trifluoromethyl-4'-iododiphenylmethane used as a starting material was obtained using the procedures described in Example 1 for the preparation of 4-fluoro-4'-iododiphenylmethane except that 4-trifluoromethylbenzaldehyde was used in place of 4-fluorobenzaldehyde.

f. The product gave the following characteristic NMR signals: 1.95(m, 4H), 2.95(s, 3H), 3.8(m, 4H), 4.15(s, 2H), 7.1-7.8(m, 15H).

The 4-(2-naphthyl)-4'-iododiphenylmethane used as a starting material was obtained using the procedures described in Example 1 for the preparation of 4-fluoro-4'-iododiphenylmethane except that 2-naphthaldehyde was used in place of 4-fluorobenzaldehyde.

g. The product gave the following characteristic NMR signals: 1.6(d, 3H), 1.95(m, 4H), 2.95(s, 3H), 3.8(m, 4H), 4.1(q, 1H), 6.9-7.4(m, 12H).

The 1-(4-fluorophenyl)-1-(4-iodophenyl)ethane used as a starting material was obtained using the procedures described in Example 1 for the preparation of 4-fluoro-4'-iododiphenylmethane except that 4-fluoroacetophenone was used in place of 4-fluorobenzaldehyde.

h. The product gave the following characteristic NMR signals: 1.95(m, 4H), 2.95(m, 3H), 3.8(m, 4H), 5.5(s, 1H), 7.0-7.4(m, 18H).

The 4-iodotriphenylmethane used as a starting material was obtained using the procedures described in Example 1 for the preparation of 4-fluoro-4'-iododiphenylmethane except that benzophenone was used in place of 4-fluorobenzaldehyde.

i. The product gave the following characteristic NMR signals: 1.95(m, 4H), 2.95(s, 3H), 3.8(m, 4H), 7.2-7.4(m, 13H).

The 4-iododiphenyl sulphide used as a starting material was obtained as follows:

A mixture of 1,4-diiodobenzene (5 g), benzenethiol (0.78 ml), cuprous chloride (0.2 g), potassium carbonate (1.05 g) and DMF (10 ml) was heated to 120° C. for 90 minutes. The mixture was cooled to ambient temperature and partitioned between water and diethyl ether. The organic phase was washed with water and with brine, dried (MgSO4) and evaporated. The residue was purified by column chromatography using hexane as eluent. There was thus obtained the required starting material as an oil (1.5 g).

NMR Spectrum 7.0(d, 2H), 7.2-7.4(m, 5H), 7.6(d, 2H).

j. The product gave the following characteristic NMR signals: 2.0(m, 4H), 2.95(s, 3H), 3.8(m, 4H), 7.2–8.0(m, 13H).

The 4-iododiphenyl sulphone used as a starting material was obtained as follows:

A mixture of 4-iododiphenyl sulphide (0.5 g), potassium peroxymonosulphate (0.59 g), ethanol (5 ml) and water (5 ml) was stirred at ambient temperature for 18 hours. The mixture was partitioned between chloroform and water. The organic phase was washed with brine, dried (MgSO$_4$) and evaporated. The residue was purified by medium pressure chromatography using increasingly polar mixtures of hexane and ethyl acetate as eluent. There was thus obtained the required starting material (0.33 g), m.p. 129°–131° C.

k. The product gave the following characteristic NMR signals: 1.95(m, 4H), 2.95(s, 3H), 3.8(m, 4H), 5.0(s, 2H), 6.8–7.0(m, 4H), 7.2–7.4(m, 8H).

The 4-fluorophenyl 4-iodobenzyl ether used as a starting material was obtained as follows:

Sodium hydride (60% w/w dispersion in mineral oil, 0.07 g) was added to a mixture of 4-fluorophenol (0.19 g) and DMF (3 ml) and the mixture was stirred at ambient temperature for 1 hour. 4-Iodobenzyl bromide (0.5 g) was added and the mixture was stirred at ambient temperature for 18 hours. The mixture was partitioned between diethyl ether and water. The organic phase was washed with brine, dried (MgSO$_4$) and evaporated. The residue was purified by medium pressure chromatography on reverse-phase silica using decreasingly polar mixtures of water and methanol as eluent. There was thus obtained the required starting material (0.25 g), m.p. 63°–64° C.

NMR Spectrum 4.95(s, 2H), 6.8–7.0(m, 4H), 7.2(d, 2H), 7.7(d, 2H).

l. The product gave the following characteristic NMR signals: 2.0(m, 4H), 3.0(s, 3H), 3.8(m, 4H), 7.1–7.5(m, 12H).

The difluoro-(4-fluoro-4'-iododiphenyl)methane used as a starting material was obtained as follows:

Pyridinium chlorochromate (6 g) was added to a mixture of 4-fluoro-4'-iododiphenylmethanol (6.7 g), silica (10 g) and methylene chloride (60 ml) and the mixture was stirred at ambient temperature for 60 minutes. Diethyl ether (20 ml) was added and the mixture was filtered. The filtrate was evaporated and the residue was recrystallised from a mixture of hexane and ethyl acetate. There was thus obtained 4-fluoro-4'-iodobenzophenone (3.9 g).

NMR Spectrum 7.1–7.3(m, 2H), 7.5(m, 2H), 7.7–7.9(m, 4H).

Ethane-1,2-dithiol (1.14 g) and boron trifluoride diacetate (1.14 g) were added in turn to a solution of 4-fluoro-4'-iodobenzophenone (2 g) in methylene chloride (5 ml) and the mixture was stirred at ambient temperature for 1 hour. Hexane (20 ml) and diethyl ether (5 ml) were added and the solution was extracted with N sodium hydroxide solution (3×20 ml). The organic phase was washed with water, dried (MgSO$_4$) and evaporated. The residue was purified by medium pressure liquid chromatography using increasingly polar mixtures of hexane and ethyl acetate as eluent. There was thus obtained 2-(4-fluorophenyl)-2-(4-iodophenyl)-1,3-dithiolane as an oil (2.3 g).

NMR Spectrum 3.45(s, 4H), 7.0(m, 2H), 7.4(d, 2H), 7.5–7.7(m, 4H).

Hydrogen fluoride-pyridine complex (1 ml) and a portion (0.8 g) of the dithiolane so obtained were added in turn to a solution of 1,3-dibromo-4,4-dimethyl-2,5-dioxoimidazolidine (0.58 g) in methylene chloride (5 ml) which had been cooled to −80° C. The mixture was stirred at −80° C. for 20 minutes. Hexane (30 ml) was added and the mixture was allowed to warm to ambient temperature. The mixture was filtered through a column of alumina using increasingly polar mixtures of hexane and diethyl ether as eluent. The product so obtained was purified by medium pressure liquid chromatography on silica using increasingly polar mixture of hexane and ethyl acetate as eluent. There was thus obtained the required starting material as an oil. (0.25 g).

NMR Spectrum 7.0–7.3(m, 4H), 7.45(m, 2H), 7.8(m, 2H).

m. The product gave the following characteristic NMR signals: 1.95(m, 4H), 2.95(s, 3H), 3.8(m, 4H), 5.3(s, 1H), 7.2–7.4(m, 18H).

The 4-iodotriphenylmethanol used as a starting material was obtained using the procedure described in Example 1 for the preparation of 4-fluoro-4'-iododiphenylmethanol except that benzophenone was used in place of 4-fluorobenzaldehyde.

EXAMPLE 3

Sodium borohydride (0.1 g) was added to a solution of 4-[3-(4-benzoylphenylthio)phenyl]-4-methoxytetrahydropyran (0.16 g) in isopropanol (2 ml) and the mixture was stirred at ambient temperature for 24 hours. The mixture was partitioned between diethyl ether and water. The organic layer was washed with brine, dried (MgSO$_4$) and evaporated. The residue was recrystallised from a mixture of diethyl ether and hexane. There was thus obtained 4-[3-(4-(alpha-hydroxybenzyl)phenylthio)phenyl]-4-methoxytetrahydropyran (0.08 g, 50%), m.p. 99°–100° C.

NMR Spectrum 1.95(m, 4H), 2.09(s, 3H), 3.8(m, 4H), 5.8(s, 1H), 7.2–7.4(m, 13H).

The 4-[3-(4-benzoylphenylthio)phenyl]-4-methoxytetrahydropyran used as a starting material is described in copending European Patent Application No. 90306765.0 (Example 26, compound no. 3 therein).

EXAMPLE 4

A solution of 4-[3-(4-(4-fluorobenzoyl)phenylthio)phenyl]-4-methoxytetrahydropryan (0.13 g) in THF (2 ml) was added to a solution of methyl magnesium iodide (4 equivalents) in diethyl ether (3 ml) and the mixture was stirred at ambient temperature for 30 minutes. The mixture was poured onto a saturated aqueous ammonium chloride solution and extracted with diethyl ether (2×20 ml). The organic extract was washed with brine, dried (MgSO$_4$) and evaporated. The residue was purified by medium pressure liquid chromatography using increasingly polar mixtures of hexane and ethyl acetate as eluent. There was thus obtained 4-[3-(4-[1-(4-fluorophenyl)-1-hydroxyethyl]phenylthio)phenyl]-4-methoxytetrahydropyran (0.055 g, 40%), m.p. 104°–107° C.

NMR Spectrum (CD$_3$SOCD$_3$) 1.8(m, 4H), 2.81(s, 3H), 3.25(s, 3H), 3.65(m, 4H), 5.8(s, 1H), 7.0–7.5(m, 12H).

The 4-[3-(4-(4-fluorobenzoyl)phenylthio)phenyl]-4-methoxytetrahydropyran used as a starting material was obtained by the reaction of 4-fluoro-4'-iodobenzophenone with 4-(3-mercaptophenyl)-4-methoxytetrahydropyran using the procedure described in Example 1. There was thus obtained the required starting material in 46% yield, m.p. 102°–103° C.

NMR Spectrum 2.0(m, 4H), 3.0(s, 3H), 3.85(m, 4H), 7.1–7.9(m, 12H).

EXAMPLE 5

Sodium hydride (60% w/w dispersion in mineral oil, 0.06 g) was added to a solution of 4-[3-(4-[1-(4-fluorophenyl)-1-hydroxyethyl]phenylthio)phenyl]-4-methoxytetrahydropyran (0.19 g) in DMF (2 ml) and the mixture was stirred at ambient temperature for 1 hour. Methyl iodide (0.33 g) was added and the mixture was stirred at ambient temperature for 3 hours. The mixture was partitioned between diethyl ether and water. The organic phase was washed with brine, dried (MgSO4) and evaporated. The residue was purified by medium pressure liquid chromatography using increasingly polar mixtures of hexane and ethyl acetate as eluent. There was thus obtained 4-[3-(4-[1-(4-fluorophenyl)-1-methoxyethyl]phenylthio)phenyl]-4-methoxytetrahydropyran as an oil (0.11 g, 50%).

NMR Spectrum (CD3SOCD3) 1.85(m, 7H), 2.8(s, 3H), 3.1(s, 3H), 3.65(m, 4H), 7.1–7.4(m, 12H).

EXAMPLE 6

Using the procedure described in Example 1, 4-fluoro-4'-iododiphenylmethane was reacted with (2S,4R)-4-(3-mercaptophenyl)-4-methoxy-2-methyltetrahydropyran to give (2S,4R)-4-[3-(4-(4-fluorobenzyl)phenylthio)phenyl]-4-methoxy-2-methyltetrahydropyran in 51% yield as an oil.

NMR Spectrum 1.2(d, 3H), 1.55(m, 1H), 1.9(m, 3H), 2.95(s, 3H), 3.9(m, 5H), 7.0–7.4(m, 12H).

The (2S,4R)-4-(3-mercaptophenyl)-4-methoxy-2-methyltetrahydropyran used as a starting material is described in European Patent Application No. 90310332.3 (published as European Patent Application No. 0420511).

EXAMPLE 7

Using a similar procedure to that described in Example 1, except that 4-(5-fluoro-3-mercaptophenyl)-4-methoxytetrahydropyran was used in place of 4-(3-mercaptophenyl)-4-methoxytetrahydropyran, there was obtained 4-[5-fluoro-3-(4-[4-fluorobenzyl]phenylthio)phenyl]-4-methoxytetrahydropyran in 18% yield, m.p. 62°–64° C.

NMR Spectrum 1.8–2.0(m, 4H), 2.9(s, 3H), 3.8(m, 4H), 3.95(s, 2H), 6.9–7.4(m, 11H).

The 4-(5-fluoro-3-mercaptophenyl)-4-methoxytetrahydropyran used as a starting material is described in European Patent Application No. 90310332.3 (Example 4 thereof; published as European Patent Application No. 0420511).

EXAMPLE 8

A mixture of 1-(4-iodobenzyl)pyrrole, 4-(3-mercaptophenyl)-4-methoxytetrahydropyran (0.1 g), cuprous chloride (0.025 g), potassium carbonate (0.062 g) and DMF (0.5 ml) was heated to 120° C. for 90 minutes. The mixture was cooled to ambient temperature and partitioned between water and diethyl ether. The organic phase was washed with water and with brine, dried (MgSO4) and evaporated. The residue was purified by medium pressure liquid chromatography using increasingly polar mixtures of hexane and ethyl acetate as eluent. There was thus obtained 4-methoxy-4-[3-(4-(pyrrol-1-ylmethyl)phenylthio)phenyl]tetrahydropyran as a gum (0.07 g, 40%).

NMR Spectrum 1.95(m, 4H), 2.95(s, 3H), 3.8(m, 4H), 5.05(s, 2H), 6.2(t, 2H), 6.7(t, 2H), 7.0–7.4(m, 8H).

The 1-(4-iodobenzyl)pyrrole used as a starting material was obtained as follows:

Sodium hydride (60% w/w dispersion in mineral oil, 0.07 g) was added to a solution of pyrrole (0.12 ml) in DMF (3 ml) and the mixture was stirred at ambient temperature for 1 hour. 4-Iodobenzyl bromide (0.5 g) was added and the mixture was heated to 100° C. for 18 hours. The mixture was cooled to ambient temperature and partitioned between diethyl ether and water. The organic phase was washed with brine, dried (MgSO4) and evaporated. The residue was purified by medium pressure chromatography using increasingly polar mixtures of hexane and ethyl acetate as eluent. There was thus obtained the required starting material (0.12 g), m.p. 58°–50° C.

EXAMPLE 9

Using a similar procedure to that described in Example 8 except that the appropriate iodobenzene was used in place of 1-(4-iodobenzyl)pyrrole there was obtained the compounds described in the following table:

TABLE II

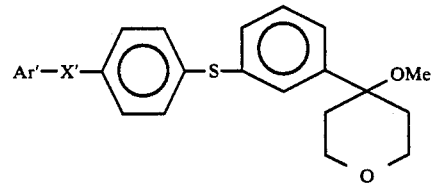

| Ex. 9 Compd. No. | Ar¹ | X¹ | m.p. (°C.) | Yield (%) |
|---|---|---|---|---|
| 1a | 1-pyrazolyl | CH2 | oil | 20 |
| 2b | 4-oxo-1,4-dihydro-pyrid-1-yl | CH2 | oil | 50 |
| 3c | 2-oxo-1,2-dihydro-pyrid-1-yl | CH2 | oil | 55 |
| 4d | 3-pyridyl | CO | 71–73 | 33 |
| 5e | 3-pyridyl | direct link | oil | 25 |

Notes a. The product was purified by reverse-phase medium pressure liquid chromatography using decreasingly polar mixtures of water and methanol as eluent. The product gave the following characteristic NMR signals: 1.95(m, 4H), 2.95(s, 3H), 3.8(m, 4H), 5.3(s, 2H), 6.3(t, 1H), 7.1(d, 2H), 7.3(m, 5H), 7.4(m, 2H), 7.55(d, 1H).

The 1-(4-iodobenzyl)pyrazole used as a starting material was obtained using the procedures described in the portion of Example 8 which is concerned with the preparation of starting materials except that pyrazole was used in place of pyrrole and the reaction mixture was stirred at ambient temperature for 18 hours rather than being heated to 100° C.

b. The product was purified by medium pressure liquid chromatography using increasingly polar mixtures of chloroform and methanol as eluent. The product gave the following characteristic NMR signals: 1.95(m, 4H), 3.0(s, 3H) 3.8(m, 4H), 4.9(s, 2H), 6.4(m, 2H), 7.3(d, 2H), 7.2–7.5(m, 8H).

The 1-(4-iodobenzyl)-4-oxo-1,4-dihydropyridine used as a starting material was obtained using the procedures described in the portion of Example 8 which is concerned with the preparation of starting materials except that 4-pyridone was used in place of pyrrole.

c. The product gave the following characteristic NMR signals: 1.85(m, 4H), 2.8(s, 3H), 3.7(m, 4H), 5.1(s, 2H), 6.2(m, 1H), 6.4(d, 1H), 7.2(m, 1H), 7.2–7.4(m, 8H), 7.8(m, 1H).

The 1-(4-iodobenzyl)-2-oxo-1,2-dihydropyridine used as a starting material was prepared as described in Note b. immediately above except that 2-pyridone was used in place of 4-pyridone.

d. 4-Bromophenyl 3-pyridyl ketone was used in place of an iodobenzene.

e. 3-(4-Bromophenyl)pyridine was used in place of an iodobenzene. The product gave the following characteristic NMR signals: 1.95(m, 4H), 3.0(s, 3H), 3.85(m, 4H), 7.2–7.6(m, 9H), 7.85(m, 1H), 8.6(broad d, 1H), 8.85(broad s, 1H).

The 3-(4-bromophenyl)pyridine used as a starting material was obtained as follows:

A mixture of diethyl(3-pyridyl)borane (1 g), 1,4-dibromobenzene (2.4 g), tetrakis(triphenylphosphine)-palladium (0) (0.42 g), tetrabutylammonium bromide (0.23 g), potassium hydroxide (1.18 g) and THF (10 ml) was heated to reflux for 5 hours. The mixture was poured into water (10 ml) and extracted with ethyl acetate (2×20 ml). The combined extracts were washed with brine, dried (MgSO4) and evaporated. The residue was purified by column chromatography using increasingly polar mixtures of hexane and ethyl acetate as eluent. There was thus obtained the required starting material (0.42 g).

NMR Spectrum 7.35(m, 1H), 7.45(d, 2H), 7.6(d, 2H), 7.85(m, 1H), 8.6(q, 1H), 8.85(d, 1H).

EXAMPLE 10

Using a similar procedure to that described in Example 1, difluoro-(4-fluoro-4'-iododiphenyl)methane was reacted with 4-(5-fluoro-3-mercaptophenyl)-4-methoxytetrahydropyran to give 4-[5-fluoro-3-(4-(4-fluoro-alpha,alpha-difluorobenzyl)phenylthio)phenyl]-4-methoxytetrahydropyran in 85% yield, m.p. 54°–57° C. (recrystallised from a mixture of hexane and ethyl acetate).

EXAMPLE 11

Using a similar procedure to that described in Example 1 except that the appropriate iodobenzene was used in place of 4-fluoro-4'-iododiphenylmethane there were obtained the compounds described in the following table:

TABLE III

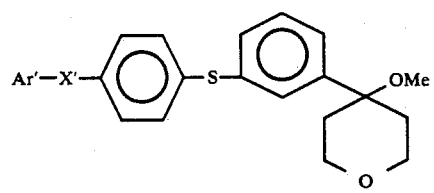

| Ex. 11 Compd. No. | Ar¹ | X¹ | m.p. (°C.) | Yield (%) |
|---|---|---|---|---|
| 1ᵃ | 4-fluorophenyl | S | gum | 11 |
| 2ᵇ | 4-fluorophenyl | SO₂ | 138–140 | 22 |

Notes a. The product gave the following characteristic NMR signals: 1.9(m, 4H), 2.95(s, 3H), 3.8(m, 4H), 7.0–7.5(m, 12H).

The 4-fluoro-4'-iododiphenyl sulphide used as a starting material was obtained as follows:

A mixture of 1,4-diiodobenzene (10 g), 4-fluorobenzenethiol (2 g), cuprous chloride (0.15 g), potassium carbonate (2.15 g) and DMF (10 ml) was stirred and heated to 120° C. for 2 hours. The mixture was cooled to ambient temperature and partitioned between water and diethyl ether. The organic phase was washed with water and with brine, dried (MgSO4) and evaporated. The residue was purified by column chromatography using hexane as eluent. There was thus obtained the required starting material (2.4 g, 49%), m.p. 49°–51° C.

NMR Spectrum 7.0(m, 4H), 7.4(m, 2H), 7.6(d, 2H).

b. The product gave the following characteristic NMR signals: (CD3SOCD3) 1.9(m, 4H), 2.85(s, 3H), 3.7(m, 4H), 7.3(d, 2H), 7.5(m, 6H), 7.85(d, 2H), 8.0(m, 2H).

4,4'-Difluorodiphenyl sulphone, used in place of an iodobenzene, was obtained as follows:

The procedure described in Note a. immediately above was repeated except that 4-fluoroiodobenzene was used in place of 1,4-diiodobenzene. There was thus obtained 4,4'-difluorodiphenyl sulphide in 77% yield.

NMR Spectrum (CD3SOCD3) 7.2(m, 4H), 7.6(m, 4H).

A mixture of the product so obtained (2 g), potassium peroxymonosulphate (11 g), ethanol (30 ml) and water (30 ml) was stirred at ambient temperature for 18 hours. The mixture was partitioned between ethyl acetate and water. The organic phase was washed with water, dried (Na2SO4) and evaporated. There was thus obtained the required starting material (1.7 g, 70%).

NMR Spectrum (CD3SOCD3) 7.5(m, 4H), 8.1(m, 4H).

EXAMPLE 12

A mixture of 4-[3-(4-(4-fluorophenylsulphonyl)-phenylthio)phenyl]-4-methoxytetrahydropyran (0.06 g), potassium peroxymonosulphate (0.13 g), ethanol (1 ml) and water (1 ml) was stirred at ambient temperature for 18 hours. The mixture was partitioned between ethyl acetate and water. The organic phase was washed with water and with brine, dried (Na2SO4) and evaporated. The residue was purified by column chromatography using increasingly polar mixtures of hexane and ethyl acetate as eluent. There was thus obtained 4-[3-(4-(4-fluorophenylsulphonyl)phenylsulphonyl)phenyl]-4-methoxytetrahydropyran (0.025 g, 40%), m.p. 170°–172° C.

NMR Spectrum 1.95(m, 4H), 2.95(s, 3H), 3.8(m, 4H), 7.2(t, 2H), 7.55(t, 1H), 7.65(m, 1H), 7.95(m, 3H), 8.05(s, 4H).

EXAMPLE 13

Using a similar procedure to that described in Example 1, 2-chloro-4'-fluoro-4-iododiphenylmethane was reacted with 4-(3-mercaptophenyl)-4-methoxytetrahydropyran to give 4-[3-(3-chloro-4-(4-fluorobenzyl)-phenylthio)phenyl]-4-methoxytetrahydropyran in 54% yield as a gum.

NMR Spectrum 1.95(m, 4H), 2.95(s, 3H), 1.8(m, 4H), 4.05(s, 2H), 6.9–7.2(m, 5H), 7.3(m, 5H), 7.45(s, 1H).

The 2-chloro-4'-fluoro-4-iododiphenylmethane used as a starting material was obtained as follows:

A mixture of 2-chloro-4-nitrobenzoic acid (10 g) and thionyl chloride (60 ml) was heated to reflux for 1 hour. The mixture was evaporated, fluorobenzene (10 ml) was added and the mixture was again evaporated. The residue was added portionwise to a mixture of fluorobenzene (75 ml) and aluminium chloride (7.3 g) and the resultant mixture was heated to reflux for 16 hours. The mixture was evaporated and the residue was poured onto ice and extracted with ethyl acetate (3×50 ml). The combined extracts were washed with water and with a saturated aqueous sodium bicarbonate solution, dried (Na$_2$SO$_4$) and evaporated. The residue was crystallised from a mixture of ethyl acetate and hexane to give 2-chloro-4'-fluoro-4-nitrobenzophenone (8.39 g, 60%) m.p. 83°–84° C.

NMR Spectrum (CD$_3$SOCD$_3$) 7.4(t, 2H), 7.8(m, 3H), 8.35(d, 1H), 8.5(d, 1H).

A mixture of a portion (4 g) of the material so obtained, iron powder (5 g), concentrated hydrochloric acid (0.5 ml), ethanol (40 ml) and water (6 ml) was heated to reflux for 3 hours. The mixture was cooled to ambient temperature, filtered and evaporated. The residue was recrystallised from a mixture of ethanol and water. There was thus obtained 4-amino-2-chloro-4'-fluorobenzophenone (2.7 g, 77%).

NMR Spectrum (CD$_3$SOCD$_3$) 6.0(broad s, 2H), 6.55(q, 1H), 6.65(d, 1H), 7.15(d, 1H), 7.3(m, 2H), 7.7(m, 2H).

A solution of sodium nitrite (0.6 g) in water (4 ml) was added dropwise to a stirred solution of a portion (2 g) of the material so obtained in a mixture of concentrated hydrochloric acid (20 ml) and water (4 ml) which had been cooled to 0° to 5° C. The mixture was stirred at 0° to 5° C. for 15 minutes and then added to a stirred solution of potassium iodide (3.2 g) in water (20 ml) which had been cooled to 0° to 5° C. The mixture was allowed to warm to ambient temperature and was stirred for 16 hours. The mixture was extracted with ethyl acetate (3×40 ml). The combined extracts were washed with a dilute aqueous sodium hydroxide solution, with water, with a saturated aqueous sodium bisulphite solution and with water, dried (Na$_2$SO$_4$) and evaporated. The residue was purified by column chromatography using increasingly polar mixtures of hexane and ethyl acetate as eluent. The brown gum so obtained was triturated under hexane. There was thus obtained 2-chloro-4'-fluoro-4-iodobenzophenone as a white solid (1.24 g, 43%), m.p. 64°–65° C.

NMR Spectrum (CD$_3$SOCD$_3$) 7.3(d, 1H), 7.4(t, 2H), 7.8(q, 2H), 7.9(q, 1H), 8.05(d, 1H).

Pyridine-borane complex (0.2 ml, 2 equivalents) was added to a solution of a portion (0.384 g) of the material so obtained in trifluoroacetic acid (2 ml) and the mixture was stirred at ambient temperature for 16 hours and then heated to reflux for 40 minutes. The mixture was cooled to ambient temperature and evaporated. The residue was basified by the addition of a strong aqueous sodium hydroxide solution and the aqueous mixture was heated to 120° C. for 30 minutes. The mixture was cooled to ambient temperature and extracted with diethyl ether (3×30 ml). The combined extracts were washed with water, dried (Na$_2$SO$_4$) and evaporated. The residue was purified by column chromatography using increasingly polar mixtures of hexane and ethyl acetate as eluent. There was thus obtained the required starting material (0.2 g, 62%).

NMR Spectrum 4.0(s, 2H), 6.85(d, 1H), 7.0(t, 2H), 7.1(m, 2H), 7.5(q, 1H), 7.7(d, 1H).

EXAMPLE 14

Using a similar procedure to that described in Example 1 except that the appropriate iodobenzene was used in place of 4-fluoro-4'-iododiphenylmethane and that 4-(5-fluoro-3-mercaptophenyl)-4-methoxytetrahydropyran was used in place of 4-(3-mercaptophenyl-4-methoxytetrahydropyran there was thus obtained the compounds described in the following table:

TABLE IV

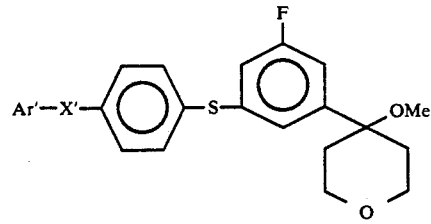

| Ex. 14. Comp. No. | Ar$^1$ | X$^1$ | m.p. (°C.) | Yield (%) |
|---|---|---|---|---|
| 1$^a$ | 4-cyanophenyl | CH$_2$ | 121–125 | 18 |
| 2$^b$ | 4-dimethylaminophenyl | CH$_2$ | oil | 12 |
| 3$^c$ | 4-(2-dimethylaminoethoxy)phenyl | CH$_2$ | oil | 13 |
| 4$^d$ | phenyl | O | oil | 65 |
| 5$^e$ | 4-fluorophenyl | O | oil | 8 |
| 6$^f$ | phenyl | NH | 95–97 | 77 |

Notes: a–f a. The 4-cyano-4'-iododiphenylmethane used as a starting material was obtained using the procedures described in Example 1 for the preparation of 4-fluoro-4'-iododiphenylmethane except that 4-cyanobenzaldehyde was used in place of 4-fluorobenzaldehyde. There was thus obtained the required starting material in 29% yield.

NMR Spectrum 4.0(s, 2H), 6.9–7.9(m, 8H).

b. The product gave the following characteristic NMR signals: 2.40(m, 4H), 2.90(s, 6H), 2.95(s, 3H), 3.80(m, 4H), 3.90(s, 2H), 6.6–7.4(m, 11H).

The 4-dimethylamino-4'-iododiphenylmethane used as a starting material was obtained from 4-dimethylaminobenzaldehyde using analogous procedures to those described in Example 1 for the preparation of 4-fluoro-4'-iododiphenylmethane. There was thus obtained the required starting material in 24% yield.

NMR Spectrum 2.90(s, 6H), 3.80(s, 2H), 6.6–7.6(m, 8H).

c. The product gave the following characteristic NMR signals: 1.90(m, 4H), 2.50(s, 6H), 3.00(s, 5H), 3.80(m, 4H), 3.95(s, 2H), 4.20(t, 2H), 6.9–7.4(m, 11H).

The 4-(2-dimethylaminoethoxy)-4'-iododiphenylmethane used as a starting material was obtained as follows:

4-Iodobenzoyl chloride (39.9 g) was added portionwise to a stirred mixture of phenol (14.1 g), triethylamine (210 ml) and methylene chloride (900 ml) which was cooled to 10° C. The mixture was stirred at ambient temperature for 1 hour. The mixture was partitioned between methylene chloride and water. The organic phase was washed with water and with a saturated aqueous sodium bicarbonate solution, dried (MgSO$_4$) and evaporated. There was thus obtained phenyl 4-iodobenzoate (17.45 g, 40%).

A mixture of the product so obtained, aluminum trichloride (10.8 g) and nitrobenzene (175 ml) was stirred and heated to 60° C. for 48 hours. The mixture was cooled to ambient temperature, poured onto 3N aqueous hydrochloric acid solution (300 ml) and extracted with diethyl ether (3×200 ml). The combined extracts were washed with 2N aqueous sodium hydroxide solution (5×250 ml). The combined aqueous extracts were cooled and acidified by the addition of concentrated hydrochloric acid. The solution was extracted with diethyl ether (3×200 ml). The combined extracts were washed with water, dried (MgSO$_4$) and evaporated. The residue was recrystallised from a mixture of hexane and acetone. There was thus obtained 4-hydroxy-4'-iodobenzophenone (7.4 g, 43%).

NMR Spectrum 5.8(broad s, 1H), 6.7-7.9(m, 8H).

Sodium borohydride (3.33 g) was added portionwise to a solution of the product so obtained in methanol (160 ml) which was cooled to 5° C. and the mixture was stirred at 5° C. for 75 minutes. Water (10 ml) was added dropwise and the mixture was extracted with diethyl ether (3×200 ml). The combined extracts were washed with water, dried (MgSO$_4$) and evaporated. There was thus obtained 4-hydroxy-4'-iododiphenylmethanol (4.9 g, 69%).

NMR Spectrum 5.6(s, 1H), 6.8-7.8(m, 8H).

Potassium iodide (12.45 g) and trimethylsilyl chloride (9.51 ml) were added in turn to a solution of 4-hydroxy-4'-iododiphenylmethanol (4.9 g) in acetonitrile (200 ml) and the mixture was stirred at ambient temperature for 90 minutes. The mixture was partitioned between diethyl ether and water. The organic phase was washed with a saturated aqueous sodium sulphite solution, dried (MgSO$_4$) and evaporated. The residue was purified by column chromatography using a 5:1 v/v mixture of hexane and ethyl acetate as eluent. There was thus obtained 4-hydroxy-4'-iododiphenylmethane (2.77 g, 60%).

NMR Spectrum 3.85(s, 2H), 4.6(broad s, 1H), 6.7-7.6(m, 8H).

Sodium methoxide (0.108 g) was added to a stirred solution of a portion (0.62 g) of the product so obtained in a mixture of chlorobenzene (17 ml) and ethanol (1.2 ml). The mixture was stirred vigorously and distilled until the distillate had a boiling point of 130° C. The residue was cooled to ambient temperature and a solution of 2-dimethylaminoethyl chloride (0.43 g) in toluene (40 ml) was added. The mixture was stirred and heated to reflux for 4 hours. The mixture was cooled to ambient temperature and partitioned between diethyl ether and water. The organic phase was washed with water, dried (MgSO$_4$) and evaporated. There was thus obtained 4-(2-dimethylaminoethoxy)-4'-iododiphenylmethane (0.67 g, 88%).

NMR Spectrum 2.40(s, 6H), 2.80(t, 2H), 3.85(s, 2H), 4.10(t, 2H), 6.7-7.6(m, 8H).

d. The reaction mixture was heated to 140° C. for 3 hours. The product gave the following characteristic NMR signals: 1.91(m, 4H), 2.96(s, 3H), 3.81(m, 4H), 6.70-7.46(m, 12H).

The 4-iododiphenyl ether used as a starting material was obtained as follows:

A solution of sodium nitrite (1.88 g) in water (5 ml) was added dropwise to a stirred solution of 4-phenoxyaniline (3.7 g) in a mixture of concentrated hydrochloric acid (12 ml) and water (12 ml) which had been cooled to 0° to 5° C. The mixture was stirred at 0° to 5° C. for 15 minutes and then a stirred solution of potassium iodide (4.33 g) in water (5 ml) was added, the mixture being cooled to 0° to 5° C. The mixture was allowed to warm to ambient temperature and was stirred for 2 hours. The mixture was extracted with ethyl acetate (3×40 ml). The combined extracts were washed with water, dried (Na$_2$SO$_4$) and evaporated.

The residue was purified by column chromatography using a 9:1 v/v mixture of hexane and ethyl acetate as eluent. There was thus obtained the required starting material (2.25 g, 40%).

NMR Spectrum 6.76(m, 2H), 7.01(m, 2H), 7.15(m, 1H), 7.3(m, 2H), 7.6(m, 2H).

e. 4-Bromo-4'-fluorodiphenyl ether was used rather than 4-fluoro-4'-iododiphenyl ether and the reaction mixture was heated to 140° C. for 3 hours. The product gave the following characteristic NMR signals: 1.9(m, 4H), 2.98(s, 3H), 3.8(m, 4H), 6.72(m, 1H), 6.88(m, 1H), 7.0(m, 1H), 7.45(m, 2H).

f. The reaction mixture was heated to 140° C. for 3 hours. The 4-iododiphenylamine used as a starting material is described in *Chem. Abs.*, 93, 103840y.

EXAMPLE 15

Using a similar procedure to that described in Example 1 except that the reaction was carried out at 140° C. for 3 hours, 4-bromo-2-chloro-4'-fluorodiphenyl ether was reacted with 4-(5-fluoro-3-mercaptophenyl)-4-methoxytetrahydropyran to give 4-[5-fluoro-3-(3-chloro-4-(4-fluorophenoxy)phenylthio)phenyl]-4-methoxytetrahydropyran in 14% yield as an oil.

NMR Spectrum 1.9(m, 4H), 3.0(s, 3H), 3.8(m, 4H), 6.8-7.5(m, 10H).

The 4-bromo-2-chloro-4'-fluorodiphenyl ether used as a starting material was obtained as follows:

Potassium tert-butoxide (2.44 g) was added portionwise to a stirred solution of 4-bromo-2-chlorophenol (4.15 g) in methanol (30 ml) and the mixture was stirred at ambient temperature for 30 minutes. The mixture was evaporated. 4-Nitrofluorobenzene (2.12 ml) was added and the mixture was stirred and heated to 150° C. for 1 hour. The mixture was cooled to ambient temperature and partitioned between 2N aqueous sodium hydroxide solution and diethyl ether. The organic phase was washed with water, dried (MgSO$_4$) and evaporated. There was thus obtained 4-bromo-2-chloro-4'-nitrodiphenyl ether (4.53 g, 69%), m.p. 59°-62° C.

A mixture of a portion (3.28 g) of the product so obtained, activated iron (11.4 g; obtained by stirring a mixture of iron powder and 2N aqueous hydrochloric acid for 10 minutes, filtering the mixture and washing and drying the solid), ferrous sulphate heptahydrate (1.92 g), water (60 ml) and methanol (250 ml) was stirred vigorously and heated to reflux for 4 hours. The mixture was cooled to ambient temperature, and poured into methylene chloride (1 liter). The mixture was filtered and the organic phase was washed with water, dried (MgSO$_4$) and evaporated. The residue was purified by column chromatography using a 3:1 v/v mixture of hexane and ethyl acetate as eluent. There was thus obtained 4'-amino-4-bromo-2-chlorodiphenyl ether (1.75 g, 75%), m.p. 69°-71° C.

A mixture of a portion (0.415 g) of the material so obtained and aqueous fluoroboric acid (50% w/v; 20 ml) was stirred and heated to 70° C. Sufficient glacial acetic acid was added to dissolve all of the reactants. The mixture was cooled to 0° C. forming a suspension to which was added dropwise a solution of sodium nitrite (0.11 g) in water (1 ml). The mixture was stirred at 0° C. for 30 minutes. The mixture was filtered and the precipitate was washed with diethyl ether. The solid was heated to 200° C. for 5 minutes. The black residue was partitioned between diethyl ether and water. The organic phase was washed with 2N aqueous hydrochloric acid, dried (MgSO$_4$) and evaporated. The residue was purified by column chromatography using a 5:1 v/v mixture of hexane and ethyl acetate as eluent. There was thus obtained 4-bromo-2-chloro-4'-fluorodiphenyl ether (0.194 g, 46%).

NMR Spectrum 6.8(d, 1H), 7.0(m, 4H), 7.35(m, 1H), 7.6(m, 1H).

EXAMPLE 16

A solution of 4-hydroxydiphenylether (0.372 g) in DMF (5 ml) was added to a suspension of sodium hydride (60% w/v dispersion in mineral oil, 0.08 g) in DMF (5 ml) and the mixture was stirred at ambient temperature for 15 minutes. A solution of 4-(3,5-difluorophenyl)-4-methoxytetrahydropyran (0.456 g) in DMF (5 ml) was added and the mixture was stirred and heated to 125° C. for 5 hours. The mixture was cooled to ambient temperature, poured into water (25 ml) and extracted with ethyl acetate (3×25 ml). The combined extracts were washed with water, dried (MgSO$_4$) and evaporated. The residue was purified by column chromatography using a 3:1 v/v mixture of hexane and ethyl acetate as eluent. There was thus obtained 4-[5-fluoro-3-(4-phenoxyphenoxy)phenyl]-4-methoxytetrahydropyran (0.582 g, 74%) as a liquid.

NMR Spectrum 1.95(m, 4H), 3.0(s, 3H), 3.84(m, 4H), 6.6-7.4(m, 12H).

The 4-(3,5-difluorophenyl)-4-methoxytetrahydropyran used as a starting material was obtained as follows:

A Grignard reagent was prepared from 3,5-difluorobromobenzene (38.6 g) and magnesium (4.88 g) in a mixture of toluene (100 ml) and THF (50 ml) using the following method. The 3,5-difluorobromobenzene was dissolved in toluene (50 ml) and a portion (aprox. 5%) of the solution was added to a stirred suspension of the magnesium in a mixture of toluene (50 ml) and THF (50 ml). The mixture was stirred at ambient temperature for approximately 40 minutes until the initiation of the exothermic formation of the Grignard reagent was observed. The mixture was cooled in an ice-bath to a temperature in the range 15° to 20° C. while the remainder of the solution of 3,5-difluorobromobenzene was added. The mixture was stirred at ambient temperature for 2 hours.

Tetrahydropyran-4-one (10.69 g) was added over 1 hour to a portion (100 ml) of the Grignard reagent so obtained which was cooled to a temperature in the range 15° to 20° C. The mixture was stirred at ambient temperature for 2 hours. The mixture was cooled in an ice-bath and aqueous hydrochloric acid solution (50% w/v, 25 ml) and brine (30% w/v, 52 ml) were added in turn. The toluene layer was separated and the aqueous layer was extracted with toluene (32 ml). The organic solutions were combined and washed with water (4×32 ml). The solution was evaporated under reduced pressure to a volume of 16.3 ml. There was thus obtained a concentrated (90% w/v) solution of 4-(3,5-difluorophenyl)-4-hydroxytetrahydropyran in toluene. The concentrate was warmed to 60° C. and chlorobenzene (22.25 ml) was added, the temperature being maintained at 60° C. The mixture was allowed to cool to ambient temperature and then cooled in an ice-bath to a temperature in the range 0° to 5° C. The precipitate was isolated and washed with hexane (2×10 ml). There was thus obtained 4-(3,5-difluorophenyl)-4-hydroxytetrahydropyran (12.2 g).

A portion (7.15 g) of the material so obtained was dissolved in N-methylpyrrolidin-2-one (25 ml) and added to a slurry of sodium hydride (60% w/w dispersion in mineral oil; 3.34 g) in N-methylpyrrolidin-2-one (32 ml) which was cooled in an ice-bath to approximately 20° C. The mixture was stirred at this temperature for 30 minutes. Methyl iodide (5.22 g) was dissolved in N-methylpyrrolidin-2-one (2 ml) and added to the mixture. The resultant mixture was warmed to 30° C. and stirred for 2 hours. The mixture was evaporated. There was thus obtained 4-(3,5-difluorophenyl)-4-methoxytetrahydropyran which was used without further purification.

EXAMPLE 17

Lithium aluminium hydride (1M in THF. 1.5 ml) was added dropwise to a stirred solution of 4-[3-(4-(4-cyanobenzyl)phenylthio)-5-fluorophenyl]-4-methoxytetrahydropyran (0.675 g) in THF (9 ml) and the mixture was stirred at ambient temperature for 1 hour. Water (5 ml) and 4N aqueous sodium hydroxide solution (5 ml) were added in turn. The mixture was extracted with diethyl ether. The organic phase was washed with water, dried (MgSO$_4$) and evaporated. The residue was dissolved in diethyl ether (5 ml) and a solution of oxalic acid in diethyl ether was added. The precipitate was isolated. There was thus obtained the mono-oxalate salt of 4-[3-(4-(4-aminomethylbenzyl)phenylthio)-5-fluorophenyl]-4-methoxytetrahydropyran (0.34 g), m.p. 142°-146° C.

EXAMPLE 18

A mixture of 4-[3-(4-(4-(3-dimethylaminopropoxy)-benzoyl)-phenylthio)-5-fluorophenyl]-4-methoxytetrahydropyran (0.73 g), zinc iodide (1 g), sodium cyanoborohydride (0.66 g) and 1,2-dichloroethane (30 ml) was stirred and heated to 85° C. for 2 hours. The mixture was cooled to ambient temperature and filtered. The solid was washed with 1,2-dichloroethane. The filtrate and washings were combined and evaporated. The residue was purified by column chromatography using a 2:1:0.3 v/v mixture of hexane, ethyl acetate and triethylamine as eluent. There was thus obtained 4-[3-(4-(4-(3-dimethaminopropoxy)benzyl)-phenylthio)-5-fluorophenyl]-4-methoxytetrahydropyran (0.096 g) as an oil.

NMR Spectrum 1.90(m, 6H), 2.25(s, 6H), 2.45(t, 2H), 3.00(s, 3H), 3.80(m, 4H), 3.95(m, 2H), 6.8-7.4(m, 11H).

The 4-[3-(4-(4-(3-dimethylaminopropoxy)benzoyl)-phenylthio)-5-fluorophenyl]-4-methoxytetrahydropyran used as a starting material was obtained as follows:

A mixture of 4-fluoro-4'-hydroxybenzophenone (2.16 g), 4-(5-fluoro-3-mercaptophenyl)-4-methoxytetrahydropyran (3.63 g), potassium carbonate (1.38 g) and DMF (25 ml) was stirred and heated to 120° C. for 90 minutes. The mixture was cooled to ambient temperature and partitioned between diethyl ether and water. The organic phase was washed with water, dried (MgSO$_4$) and evaporated. There was thus obtained 4-[5-fluoro-3-(4-(4-hydroxybenzoyl)phenylthio)-phenyl]-4-methoxytetrahydropyran (3.71 g, 84%).

NMR Spectrum 1.95(m, 4H), 3.0(s, 3H), 3.85(m, 4H), 6.8-7.8(m, 11H).

Sodium methoxide (0.27 g) was added to a stirred solution of a portion (2.19 g) of the product so obtained in a mixture of chlorobenzene (60 ml) and ethanol (4.2 ml). The mixture was stirred vigorously and distilled until the distillate had a boiling point of 130° C. The residue was cooled to ambient temperature and a solution of 3-dimethylaminopropyl chloride (1.22 g) in toluene (40 ml) was added. The mixture was heated to reflux for 4 hours, cooled to ambient temperature and partitioned between diethyl ether and water. The organic phase was washed with dilute aqueous sodium hydroxide solution and with water, dried (MgSO$_4$) and evaporated. There was thus obtained the required starting material (0.73 g, 28%).

NMR Spectrum 1.95(m, 6H), 2.25(s, 6H), 2.50(t, 2H), 3.0(s, 3H), 3.8(m, 4H), 4.1(t, 2H), 6.9–7.8(m, 11H).

EXAMPLE 19

Using an analogous procedure to that described in Example 1 except that the reaction mixture was heated to 120° C. for 3 hours, 4-(tert-butoxycarbonylmethoxy)-4'-iododiphenylmethane was reacted with 4-(5-fluoro-3-mercaptophenyl)-4-methoxytetrahydropyran to give 4-[3-(4-(4-tert-butoxycarbonylmethoxybenzyl) phenylthio)-5-fluorophenyl]-4-methoxytetrahydropyran in 75% yield as an oil.

NMR Spectrum 1.5(s, 9H), 1.9(m, 4H), 3.0(s, 3H), 3.8(m, 4H), 3.95(s, 2H), 4.5(s, 2H), 6.7–7.4(m, 11H).

A mixture of the product so obtained (0.387 g), trifluoroacetic acid (1.5 ml) and methylene chloride (5 ml) was stirred at 0° to 5° C. for 30 minutes and at ambient temperature for 90 minutes. The mixture was evaporated and the residue was purified by reversed-phase MPLC using a 85:15:0.1 v/v mixture of water, methanol and trifluoroacetic acid as eluent. There was thus obtained 4-[3-(4-(4-carboxymethoxybenzyl)phenylthio)-5-fluorophenyl]-4-methoxytetrahydropyran (0.128 g, 40%) as a gum.

NMR Spectrum 1.85(m, 4H), 3.0(s, 3H), 3.8(m, 4H), 3.95(s, 2H), 4.6(s, 2H), 4.7(broad hump, 1H), 6.7–7.4(m, 11H).

The 4-(tert-butoxycarbonylmethoxy)-4'-iododiphenylmethane used as a starting material was obtained as follows:

A mixture of 4-hydroxy-4'-iododiphenylmethane (1.24 g), tert-butyl 2-bromoacetate (1.29 ml), potassium carbonate (0.534 g) and acetone (40 ml) was stirred and heated to reflux for 2 hours. The mixture was cooled to ambient temperature and partitioned between diethyl ether and water. The organic phase was washed with 1N aqueous sodium hydroxide solution and with water, dried (MgSO$_4$) and evaporated. The residue was purified by column chromatography using a 19:1 v/v mixture of hexane and ethyl acetate as eluent. There was thus obtained the required starting material (1.12 g, 66%) as an oil.

NMR Spectrum 1.5(s, 9H), 3.85(s, 2H), 4.50(s, 2H), 6.8–7.6(m, 8H).

EXAMPLE 20

Using a similar procedure to that described in Example 1, except that the reaction was carried out at 130° C. for 1 hour, 2-chloro-4-dimethylamino-4'-iododiphenylmethane was reacted with 4-(5-fluoro-3-mercaptophenyl)-4-methoxytetrahydropyran to give 4-[3-(4-(2-chloro-4-dimethylaminobenzyl)phenylthio)-5-fluorophenyl]-4-methoxytetrahydropyran in 66% yield as an oil.

NMR Spectrum 1.9–2.0(m, 4H), 2.92(s, 6H), 2.95(s, 3H), 3.8(m, 4H), 4.0(s, 2H), 6.3–7.4(m, 10H).

The 2-chloro-4-dimethylamino-4'-iododiphenylmethane used as a starting material was obtained using similar procedures to those described in Example 1 for the preparation of 4-fluoro-4'-iododiphenylmethane except that 2-chloro-4-dimethylaminobenzaldehyde (French Patent Application No. 1,377,226) was used in place of 4-fluorobenzaldehyde. There was thus obtained the required starting material in 30% yield.

NMR Spectrum 2.9(s, 6H), 3.9(s, 2H), 6.5–7.6(m, 8H).

EXAMPLE 21

Using a similar procedure to that described in Example 1, except that the reaction mixture was heated to 120° C. for 3 hours, 4-(3-dimethylaminoprop-1-enyl)-4'-iododiphenyl ether was reacted with 4-(5-fluoro-3-mercaptophenyl)-4-methoxytetrahydropyran to give 4-[3-(4-(4-(3-dimethylaminoprop-1-enyl)phenoxy)phenylthio)-5-fluorophenyl]-4-methoxytetrahydropyran in 62% yield as an oil.

NMR Spectrum 1.9(m, 4H), 2.3(s, 6H), 3.0(s, 3H), 3.2(m, 2H), 3.8(m, 4H), 5.8–6.6(m's, 2H), 6.7–7.45(m, 11H).

A mixture of the product so obtained (0.394 g), 30% palladium-on-charcoal catalyst (0.2 g) and ethanol (20 ml) was stirred under an atmosphere of hydrogen for 6 hours. The mixture was filtered and the filtrate was evaporated. The residue was partitioned between methylene chloride and a saturated aqueous sodium bicarbonate solution. The organic phase was dried and evaporated. There was thus obtained 4-[3-(4-(4-(3-dimethylaminopropyl)phenoxy)phenylthio)-5-fluorophenyl]-4-methoxytetrahydropyran (0.225 g, 57%).

NMR Spectrum 1.88(m, 5H), 2.27(s, 6H), 2.3(m, 2H), 2.65(t, 2H), 2.96(s, 3H), 3.8(m, 4H), 6.68–7.44(m, 11H).

The 4-(3-dimethylaminoprop-1-enyl)-4'-iododiphenyl ether used as a starting material was obtained as follows:

Potassium tert-butoxide (3.8 g) was added to a solution of 4-iodophenol (6.6 g) in methanol (30 ml) and the mixture was stirred at ambient temperature for 30 minutes. The mixture was evaporated. A mixture of the residue so obtained, 4-fluorobenzaldehyde (3.72 g) and DMF (20 ml) was stirred and heated to 120° C. for 3 hours. The mixture was cooled to ambient temperature and partitioned between water and ethyl acetate. The organic phase was washed with 2N aqueous sodium hydroxide solution and with water, dried (MgSO$_4$) and evaporated. The residue was purified by column chromatography using a 5:1 v/v mixture of hexane and ethyl acetate as eluent. There was thus obtained 4-formyl-4'-iododiphenyl ether (3.9 g, 40%) as an oil.

n-Butyl lithium (1.6M in hexane, 2.18 ml) was added dropwise to a stirred suspension of (2-dimethylaminoethyl)triphenylphosphonium bromide (1.44 g) in THF (10 ml) which had been cooled to 0° C. The mixture was stirred at 0° C. for 30 minutes. A solution of 4-formyl-4'-iododiphenyl ether (1.13 g) in THF (15 ml) was added and the mixture was stirred at 0° C. for 15 minutes and at ambient temperature for 90 minutes. The mixture was partitioned between diethyl ether and water. The organic phase was washed with water and with brine, dried (MgSO$_4$) and evaporated. The residue was purified by column chromatography using a 9:1 v/v mixture of methylene chloride and methanol as eluent. There was thus obtained the required starting material (0.846 g, 64%) as an oil.

NMR Spectrum 2.28(d, 6H), 3.2(m, 2H), 5.7–6.5(m's, 2H), 6.7–7.7(m, 8H).

CHEMICAL FORMULAE

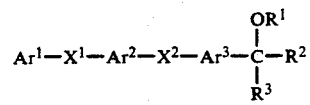

I

-continued
CHEMICAL FORMULAE

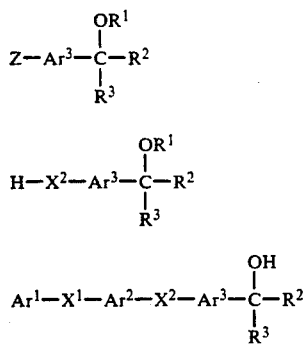

SCHEME I

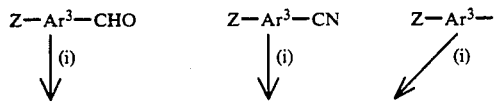

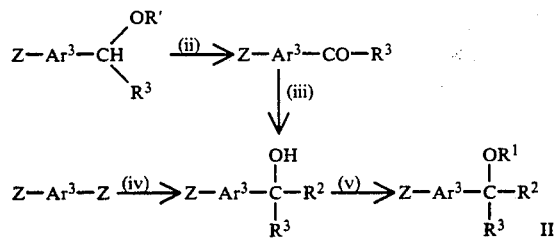

Reagents
(i) R³Li or R³MgZ, THF
(ii) DDQ or MnO₂
(iii) R²Li or R²MgZ, THF;
(iv) BuLi or Mg, THF; R²COR³, THF
(v) R¹Z, base
Note R' = (1–4C)alkyl such as Me or Et

SCHEME II

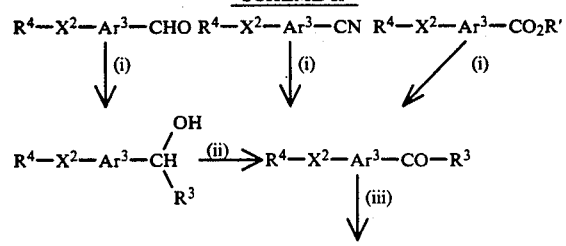

-continued
SCHEME II

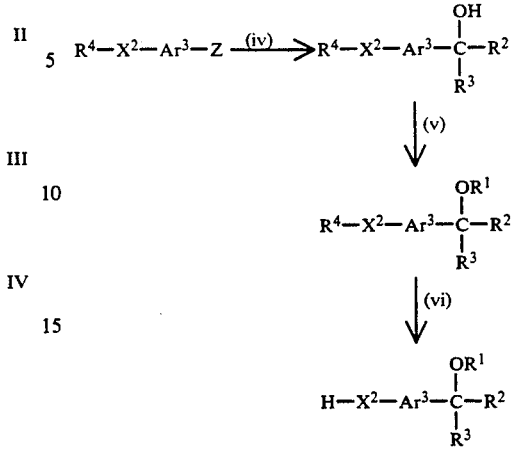

Reagents
(i) to (v) as in Scheme I
(vi) Conventional removal of the protecting group R⁴ which is, e.g, COMe, THP, CH₂Ph or Me.

SCHEME III

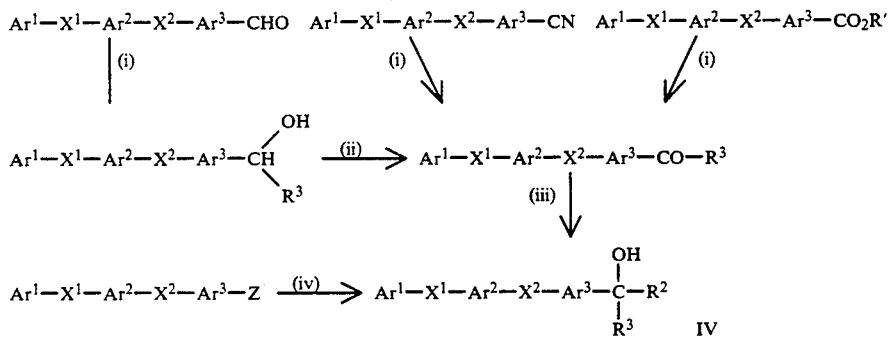

Reagents
(i) to (iv) as in Scheme I

We claim:
1. An aryl derivative of the formula I

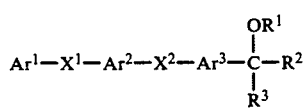

wherein Ar¹ is phenyl or naphthyl which may optionally bear one, two or three substituents selected from amino, halogeno, hydroxy, cyano, carboxy, trifluoromethyl, (1–4C)alkyl, (1–4C)alkoxy, (1–4C)alkylamino, di-[(1–4C)alkyl]amino, (1–4C)alkoxycarbonyl, amino-(1–4C)alkyl, hydroxy-(1–4C)alkyl, cyano-(1–4C)alkyl, carboxy-(1–4C)alkyl, (1–4C)alkoxycarbonyl-(1–4C)alkyl, carboxy-(1–4C)alkoxy, (1–4C)alkoxycarbonyl-(1–4C)alkoxy, amino-(2–4C)alkoxy, (1–4C)alkylamino-(2–4C)alkoxy and di-[(1–4C)alkyl]amino-(2–4C)alkoxy, and X¹ is oxy, thio, sulphinyl, sulphonyl, difluoromethylene, imino, (1–4C)alkylimino or (1–4C)alkylene and wherein the (1–4C)alkylene group may optionally bear one or two substituents selected from hydroxy, (1–4C)alkyl, (1–4C)alkoxy and phenyl, or X¹ is a group of the formula —X⁴—CR₂— or —CR₂—X⁴— wherein

X$^4$ is oxy, thio, sulphinyl, sulphonyl or carbonyl and each R, which may be the same or different, is hydrogen, methyl or ethyl;

Ar$^2$ and Ar$^3$, which may be the same or different, each is phenylene which may optionally bear one or two substituents selected from halogeno, hydroxy, amino, trifluoromethyl, (1-4C)alkyl and (1-4C)alkoxy;

X$^2$ is oxy, thio, sulphinyl or sulphonyl;

R$^1$ is (1-4C)alkyl, (3-4C)alkenyl or (3-4C)alkynyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ and A$^2$, which may be the same or different, each is (1-3C)alkylene and X$^3$ is oxy, and which ring may bear one or two substituents selected from hydroxy, (1-4C)alkyl and (1-4C)alkoxy; or a pharmaceutically-acceptable salt thereof.

2. An aryl derivative of the formula I as claimed in claim 1 wherein Ar$^1$ may optionally bear one, two or three further substituents selected from (1-4C)alkylamino-(1-4C)alkyl and di-[(1-4C)alkyl]amino-(1-4C)alkyl; or a pharmaceutically-acceptable salt thereof.

3. An aryl derivative of the formula I as claimed in claim 1 wherein Ar$^1$ is phenyl or naphthyl which may optionally bear one, two or three substituents selected from halogeno, hydroxy, cyano, carboxy, trifluoromethyl, (1-4C)alkyl, (1-4C)alkoxy, (1-4C)alkoxycarbonyl, hydroxy-(1-4C)alkyl, cyano-(1-4C)alkyl, carboxy-(1-4C)alkyl, (1-4C)alkoxycarbonyl-(1-4C)alkyl, carboxy-(1-4C)alkoxy, (1-4C)alkoxycarbonyl-(1-4C)alkoxy, amino-(2-4C)alkoxy, (1-4C)alkylamino-(2-4C)alkoxy and di-[(1-4C)alkyl]amino-(2-4C)alkoxy, and X$^1$ is oxy, thio, sulphinyl, sulphonyl, difluoromethylene or (1-4C)alkylene and wherein the (1-4C)alkylene group may optionally bear one or two substituents selected from hydroxy, (1-4C)alkyl, (1-4C)alkoxy and phenyl, or X$^1$ is a group of the formula —X$^4$—CR$_2$— or —CR$_2$—X$^4$— wherein

X$^4$ is oxy, thio, sulphinyl, sulphonyl or carbonyl and each R, which may be the same or different, is hydrogen, methyl or ethyl;

Ar$^2$ and Ar$^3$, which may be the same or different, each is phenylene which may optionally bear one or two substituents selected from halogeno, hydroxy, amino, trifluoromethyl, (1-4C)alkyl and (1-4C)alkoxy;

X$^2$ is oxy, thio, sulphinyl or sulphonyl;

R$^1$ is (1-4C)alkyl, (3-4C)alkenyl or (3-4C)alkynyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ and A$^2$, which may be the same or different, each is (1-3C)alkylene and X$^3$ is oxy, and which ring may bear one or two substituents selected from hydroxy, (1-4C)alkyl and (1-4C)alkoxy; or a pharmaceutically-acceptable salt thereof.

4. An aryl derivative of the formula I as claimed in claim 1 wherein Ar$^1$ is phenyl which may optionally bear one or two substituents selected from fluoro, chloro, hydroxy, carboxy, trifluoromethyl, methyl, ethyl, tert-butyl, methoxy, ethoxy, hydroxymethyl, 2-hydroxyprop-2-yl, carboxymethyl, 1-carboxyethyl, 2-carboxyprop-2-yl, carboxymethoxy, 1-carboxyethoxy, 2-carboxyprop-2-yloxy and 2-dimethylaminoethoxy; X$^1$ is thio, sulphinyl, sulphonyl, difluoromethylene, methylene, ethylene, hydroxymethylene, ethylidene, methoxymethylene, benzylidene, 1-hydroxy-1-methylmethylene, alpha-hydroxybenzylidene or 1-methoxy-1-methylmethylene, or X$^1$ is a group of the formula

—X$^4$—CH$_2$— wherein

X$^4$ is oxy, thio, sulphinyl or sulphonyl;

Ar$^2$ is 1,4-phenylene which may optionally bear one substituent selected from fluoro, chloro, methyl and methoxy;

X$^2$ is thio;

Ar$^3$ is 1,3-phenylene which may optionally bear one or two substituents selected from fluoro, chloro, trifluoromethyl and methyl;

R$^1$ is methyl or ethyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ is ethylene, A$^2$ is ethylene and X$^3$ is oxy, and which ring may bear one or two methyl substituents;

or a pharmaceutically-acceptable salt thereof.

5. An aryl derivative of the formula I as claimed in claim 1 wherein Ar$^1$ is phenyl which may optionally bear one or two substituents selected from fluoro, chloro, trifluoromethyl, methyl, ethyl and tert-butyl;

X$^1$ is thio, sulphinyl, sulphonyl, difluoromethylene, oxymethylene, methylene, ethylene, hydroxymethylene, ethylidene, methoxymethylene, benzylidene, 1-hydroxy-1-methylmethylene, alpha-hydroxybenzylidene or 1-methoxy-1-methylmethylene;

Ar$^2$ is 1,4-phenylene which may optionally bear one substituent selected from fluoro, chloro, methyl and methoxy;

X$^2$ is thio;

Ar$^3$ is 1,3-phenylene which may optionally bear one or two substituents selected from fluoro, chloro, trifluoromethyl and methyl;

R$^1$ is methyl or ethyl; and

R$^2$ and R$^3$ together form a group of the formula —A$^1$—X$^3$—A$^2$— which together with the carbon atom to which A$^1$ and A$^2$ are attached define a ring having 6 ring atoms, wherein A$^1$ is ethylene, A$^2$ is ethylene and X$^3$ is oxy, and which ring may bear one or two methyl substituents; or a pharmaceutically-acceptable salt thereof.

6. An aryl derivative of the formula I as claimed in claim 1 wherein Ar$^1$ is phenyl, 4-fluorophenyl, 2,4-difluorophenyl, 2,6-dichlorophenyl or 4-dimethylaminophenyl;

X$^1$ is oxy, thio, oxymethylene, methylene, ethylidene or difluoromethylene;

Ar$^2$ is 1,4-phenylene or 2-chloro-1,4-phenylene;

X$^2$ is thio;

Ar$^3$ is 1,3-phenylene or 5-fluoro-1,3-phenylene;

R$^1$ is methyl; and

R$^2$ and R$^3$ together form a group of the formula —A$^1$—X$^3$—A$^2$— which together with the carbon atom to which $A^1$ and $A^2$ is attached define a ring having 6 ring atoms, wherein $A^1$ is ethylene, $A^2$ is ethylene and $X^3$ is oxy, and which ring may bear a methyl substituent alpha to $X^3$; or a pharmaceutically-acceptable salt thereof.

7. An aryl derivative of the formula I as claimed in claim 1 wherein $Ar^1$ is 4-fluorophenyl, 2,4-difluorophenyl or 2,6-dichlorophenyl;

$X^1$ is oxymethylene, methylene, ethylidene or difluoromethylene;

$Ar^2$ is 1,4-phenylene;

$X^2$ is thio;

$Ar^3$ is 1,3-phenylene or 5-fluoro-1,3-phenylene;

$R^1$ is methyl; and $R^2$ and $R^3$ together form a group of the formula $—A^1—X^3—A^2—$ which together with the carbon atom to which $A^1$ and $A^2$ is attached define a ring having 6 ring atoms, wherein $A^1$ is ethylene, $A^2$ is ethylene and $X^3$ is oxy, and which ring may bear a methyl substituent alpha to $X^3$; or a pharmaceutically-acceptable salt thereof.

8. An aryl derivative of the formula I, or a pharmaceutically-acceptable salt thereof, as claimed in claim 1 selected from:

4-[3-(4-(4-fluorobenzyl)phenylthio)phenyl]-4-methoxytetrahydropyran,

4-[3-(4-(2,4-difluorobenzyl)phenylthio)phenyl]-4-methoxytetrahydropyran,

4-[3-(4-(4-fluoro-alpha-methylbenzyl)phenylthio)-phenyl]-4-methoxytetrahydropyran, 4-[3-(4-(4-fluorophenoxymethyl)phenylthio)phenyl]-4-methoxytetrahydropyran, 4-[5-fluoro-3-(4-(4-fluoro-alpha,alpha-difluorobenzyl)phenylthio)phenyl]-4-methoxytetrahydropyran, 4-[3-(4-(4-fluorophenylthio)phenylthio)phenyl]-4-methoxytetrahydropyran, 4-[5-fluoro-3-(4-phenoxyphenylthio)phenyl]-4-methoxytetrahydropyran and 4-[5-fluoro-3-(3-chloro-4-(4-fluorophenoxy)phenylthio)phenyl]-4-methoxytetrahydropyran.

9. A pharmaceutical composition suitable for use in providing inhibition of 5-lipoxygenase which comprises an effective amount of an aryl derivative of the formula I, or a pharmaceutically-acceptable salt thereof, as claimed in any one of claims 1 to 8 in association with a pharmaceutically-acceptable diluent or carrier.

* * * * *